(12) United States Patent
Fitzpatrick

(10) Patent No.: US 8,615,127 B2
(45) Date of Patent: Dec. 24, 2013

(54) SYSTEM AND METHOD FOR POINT-BASED RIGID REGISTRATION WITH ANISOTROPIC WEIGHTING

(75) Inventor: John Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 415 days.

(21) Appl. No.: 13/005,843

(22) Filed: Jan. 13, 2011

(65) Prior Publication Data

US 2011/0178394 A1     Jul. 21, 2011

Related U.S. Application Data

(60) Provisional application No. 61/295,212, filed on Jan. 15, 2010.

(51) Int. Cl.
*G06K 9/00*     (2006.01)

(52) U.S. Cl.
USPC ............ 382/154; 382/128; 382/218; 600/117

(58) Field of Classification Search
USPC ........................... 382/128, 154, 218; 600/117
See application file for complete search history.

(56) References Cited

U.S. PATENT DOCUMENTS

| | | | | |
|---|---|---|---|---|
| 6,252,608 | B1 * | 6/2001 | Snyder et al. ................ | 345/473 |
| 6,507,751 | B2 * | 1/2003 | Blume et al. ................. | 600/424 |
| 7,300,398 | B2 * | 11/2007 | Chefd'hotel et al. .......... | 600/117 |
| 7,906,965 | B2 * | 3/2011 | Koay ........................... | 324/312 |
| 8,395,386 | B2 * | 3/2013 | Kimura et al. ................ | 324/307 |
| 2007/0165922 | A1 * | 7/2007 | Webber et al. ................ | 382/128 |
| 2008/0262345 | A1 * | 10/2008 | Fichtinger et al. ............ | 600/426 |
| 2010/0049180 | A1 * | 2/2010 | Wells et al. ................... | 606/12 |
| 2011/0178394 | A1 * | 7/2011 | Fitzpatrick ................... | 600/424 |

OTHER PUBLICATIONS

Naoya Ohta and Kenichi Kanatani; Optimal Estimation of Three-Dimensional Rotation and Reliability Evaluation; Dept. of Computer Science, Gunma University, Kiryu, Gunma 376-8515 Japan (pp. 175-187).

Bogdan Matei and Peter Meer; Optimal Rigid Motion Estimation and Performance Evaluation With Bootstrap; Electrical and Computer Engineering Dept., Rutgers Univ., (pp. 339-345).

Mehdi Hedjazi Moghari and Purang Abolmaesumi; Point-Based Rigid-Body Registration Using and Unscented Kalman Filter, IEEE Transactions On Medical Imaging, vol. 26, No. 12, Dec. 2007 (pp. 1708-1728).

(Continued)

*Primary Examiner* — Gregory M Desire
(74) *Attorney, Agent, or Firm* — Novak Druce Connolly Bove + Quigg LLP

(57) ABSTRACT

Systems and methods for performing computer-assisted procedures are provided. In the systems and methods, a current rigid transformation is applied to a first set of points with respect to a second set of points to obtain a current transformed set of points. Thereafter, a linearized transformation is determined that minimizes a weighted fiducial registration error between the current transformed set and the second set. An updated rigid transformation is then obtained based on the current rigid transformation, the translation vector of the linearized transformation, and a rotation matrix that is closest to the linearized matrix of the linearized transformation, followed by applying the updated rigid transformation to the first set to obtain an updated transformed set of points. Finally, if motion associated with such updating fails to meet some criterion, the determining, obtaining, and applying are iteratively repeated using the updated rigid transformation and the updated transformed set.

24 Claims, 13 Drawing Sheets

(56) References Cited

OTHER PUBLICATIONS

Balachandran et al., "Fiducial registration for tracking systems that employ coordinate reference frames," Proc. SPIE Medical Imaging (2005) 5744: 134-145, San Diego, CA.

Batchelor and Fitzpatrick, "A study of the anisotropically weighted Procrustes problem," IEEE Workshop on Mathematical Methods in Biomedical Image Analysis (2000): 1-7, Hilton Head, SC.

Candocia, "Jointly registering images in domain and range by piecewise linear comparametric analysis," IEEE Trans. Image Processing (2003) 12(4): 409-419.

Farrell and Stuelpnagel, "Problem 65-1: A least squares estimate of satellite attitude," SIAM Rev 8, (1966) 384-386.

Fitzpatrick et al., "Image Registration," Medical Image Processing, in vol. II of the Handbook *of Medical Imaging*, M. Sonka and J. M. Fitzpatrick, ed., SPIE Press (2000) Chapter 8: 451-514.

Friston et al., "Spatial Registration and Normalization of images," Human Brain Mapping (1995) 2:165-189.

Koschat and Swayne, "A weighted Procrustes criterion," Psychometrika, (1991) 56(2): 229-239.

Schönemann, "A generalized solution of the orthogonal Procrustes problem," Psychometrika (1966) 31(1): 1-10.

West and Maurer, Jr., "Designing optically tracked instruments for image-guided surgery," IEEE Transactions on Medical Imaging (2004) 23: 533-545.

* cited by examiner

SYSTEM AND METHOD FOR POINT-BASED RIGID REGISTRATION WITH ANISOTROPIC WEIGHTING

CROSS REFERENCE TO RELATED APPLICATIONS

This application claims the benefit of U.S. Provisional Application Ser. No. 61/295,212 entitled "METHOD FOR POINT RIGID REGISTRATION WITH ANISOTROPIC WEIGHTING", filed Jan. 15, 2010, which is herein incorporated by reference in its entirety.

FIELD OF THE INVENTION

The present invention relates to point-based registration, and more specifically to systems and methods for point-based rigid registration with anisotropic weighting.

BACKGROUND

Point-based rigid registration is commonly used for image-guided systems. One set of points is to be registered to another set of corresponding points by means of a rigid transformation of the first set. Surgical guidance systems based on pre-operative images, such as CT or MRI, typically employ a tracking system to map points from image to the physical space of the operating room. For neurosurgery and ear surgery, because of the rigidity of the skull, the point mapping is typically a rigid transformation. The transformation is usually based on fiducial markers that are attached to the head before imaging and remain attached until the procedure begins. In general, a fiducial point set is obtained by localizing each fiducial marker both in the image and in the operating room. Then, a least-squares problem is solved to register the image points to their corresponding physical points, and the result is the rigid transformation. Typically, during such registration processes, fiducial localization error (FLE) results in registration errors, and a least-squares approach is commonly used to obtain the transformation that minimizes this error in fiducial alignment. The least-squares solution has a closed form when FLE is isotropic, but a closed form is generally unavailable in the case of anisotropic FLE, for which anisotropic weighting is required. With fiducial markers that are larger than a voxel, FLE in the image space can be made somewhat isotropic, but FLE in physical space may suffer from severe anisotropy due to tracking. For example, physical positions are often acquired via optical systems, whose localization error is highly anisotropic. Furthermore, the positions are often reckoned relative to a coordinate reference frame (CRF) that is rigidly attached to the patient. The use of a CRF enables patient movement relative to the tracking system during the procedure, but it tends to exacerbate the anisotropy.

SUMMARY

Embodiments of the invention concern systems and methods for point-based rigid registration. In the various embodiments of the invention, systems and methods for performing computer-assisted procedures, including medical procedures, are provided. In the systems and methods, a current rigid transformation is applied to a first set of points with respect to a second set of points to obtain a current transformed set of points. Thereafter, a linearized transformation is determined that minimizes a weighted fiducial registration error between the current transformed set and the second set. An updated rigid transformation is then obtained based on a rigid rotation matrix that is closest to the matrix of the linearized transformation, followed by applying the updated rigid transformation to the first set to obtain an updated transformed set of points. Finally, if motion associated with such updating fails to meet some criterion, the determining, obtaining, and applying are repeated using the updated rigid transformation and the updated transformed set.

DETAILED DESCRIPTION

Figure 1B:
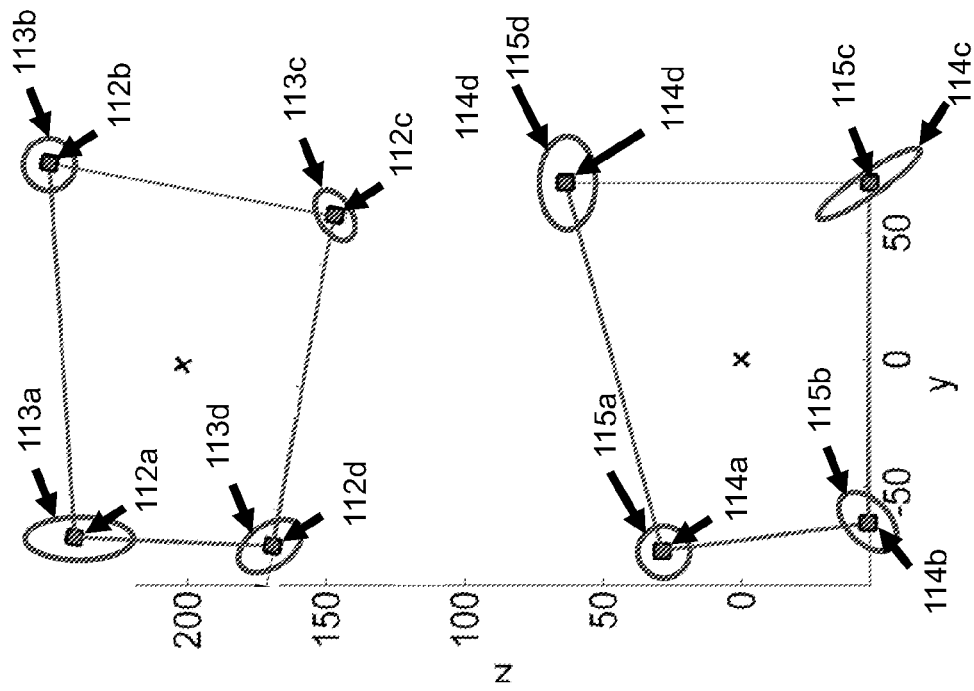
FIGS. 1A and 1B illustrate the differences between isotropic and anisotropic registration problems.

The present invention is described with reference to the attached figures, wherein like reference numerals are used throughout the figures to designate similar or equivalent elements, The figures are not drawn to scale and they are provided merely to illustrate the instant invention. Several aspects of the invention are described below with reference to example applications for illustration, it should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, rigid-body, point-based rigid registration is commonly used for image-guided systems. For example, in medical applications, fiducial markers that can be localized in two spaces: an image space associated with an image of the patient and the physical space of the patient anatomy during a procedure. The fiducial marker locations in the two spaces then serve as fiducial points that are used to obtain the physical-to-image registration. In general, it is a common practice to obtain physical positions via optical systems. However, due to errors in such optical systems or in placement of the markers in one space or another, the localization error between the spaces will generally be anisotropic.

Figure 1A:
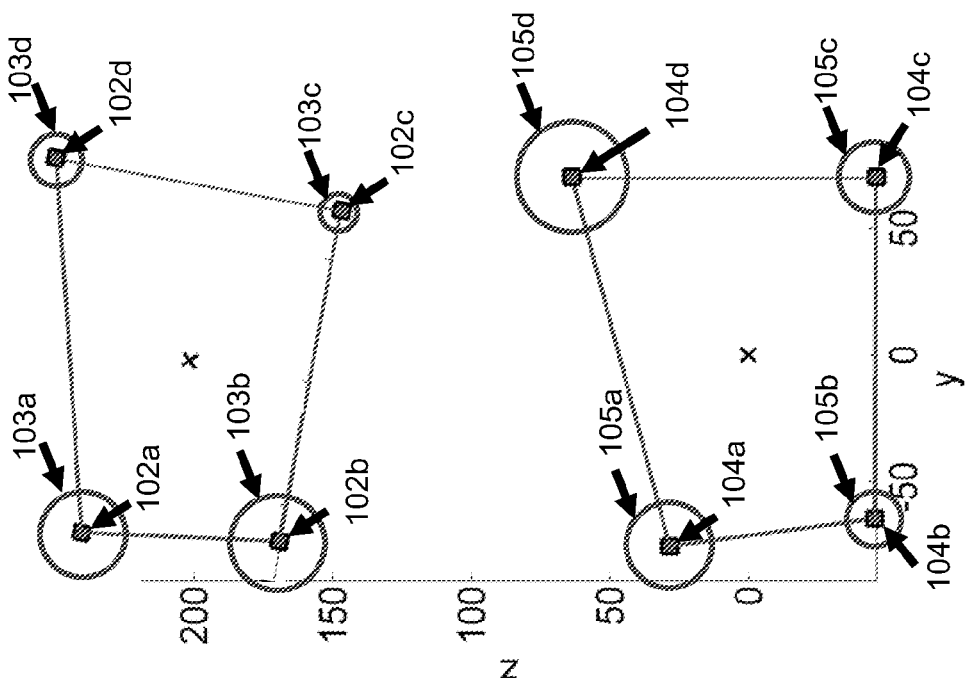

FIG. 1A shows a schematic 100 illustrating an exemplary registration problem for first set of fiducial markers 102a, 102b, 102c, and 102 defining a first space and a corresponding second set of fiducial markers 104a, 104b, 104c, and 104d defining a second space. For example, markers 102a-102d and corresponding markers 104a-104d can represent fiducial markers located on a patient and an image of a patient, or vice versa. In the case of FIG. 1, a simple rigid transformation (i.e., a rotation and a translation, with or without constant scaling) can be used to define the transformation between the locations defined by markers 102a-102d and the corresponding location defined by markers 104a-104d.

In the example described above, it is generally assumed that any errors in the placement of the markers in one space or another and/or the measurement error in locating the markers are known or have a constant variance in each direction (as shown by 103a-103d and 105a-105d). That is, the errors are either known and unknown errors are isotropic. However, in most practical scenarios, the unknown errors are generally anisotropic (i.e, different variance in different directions). In the case of a scenario similar to that of FIG. 1A, for small errors anisotropic errors, the assumption of isotropic errors and the rigid transformation described can still provide a transformation with a high degree of accuracy. However, if the anisotropic errors are sufficiently large or different, the assumption of isotropy will generally fail to provide an accurate transformation.

Further, this issue is further exacerbated when the transformation requires varying rotation, translation, and scaling with respect to different fiducials. That is, when the underlying problem is a non-rigid transformation. For example, as in the case illustrated in FIG. 1B. FIG. 1B shows a schematic 110 illustrating atypical non-rigid transformation problem for first set of fiducial markers 112a, 112b, 112c, and it 112d and a corresponding second set of fiducial markers 114a, 114b, 114c, and 114d. In such a scenario, the combination of the non-rigid transformation and any anisotropy for markers 112a-112d and 114-114b (represented by 113a-113d and 115a-115b, respectively) makes obtaining an accurate transformation a non-trivial problem.

In most conventional registration processes, it is a common practice to ignore the non-rigid transformation aspects and estimate the transformation using a rigid transformation. Further, it is common practice to ignore the localization anisotropy and employ a closed-form solution, which is available for isotropic weighting but not for anisotropic weighting. Iterative methods are also available for anisotropic weighting but are generally complex.

In view of the limitations of conventional registration systems and methods, the various embodiments provide new systems and methods for providing a point-based rigid registration. In particular, systems and methods in accordance with the various embodiments are configured to utilize a new iterative algorithm, taking into account anisotropic weighting, without the complexities of conventional anisotropic weighting algorithms. This approach can be used to provide a more accurate solution for anisotropic localization error than is typically observed for approaches utilizing a conventional isotropic solution. Thus, the new algorithm reduces target registration error when anisotropic localization error is present. Further, when all the localization errors are isotropic, the new algorithm performs as well as the closed-form solution.

In the various embodiments, the terms fiducials, fiducial points, fiducial markers, markers, and points, as used herein, are synonymous and refer to any point or any means of selecting, marking, or identifying a point in a 3-dimensional space.

Figure 2:
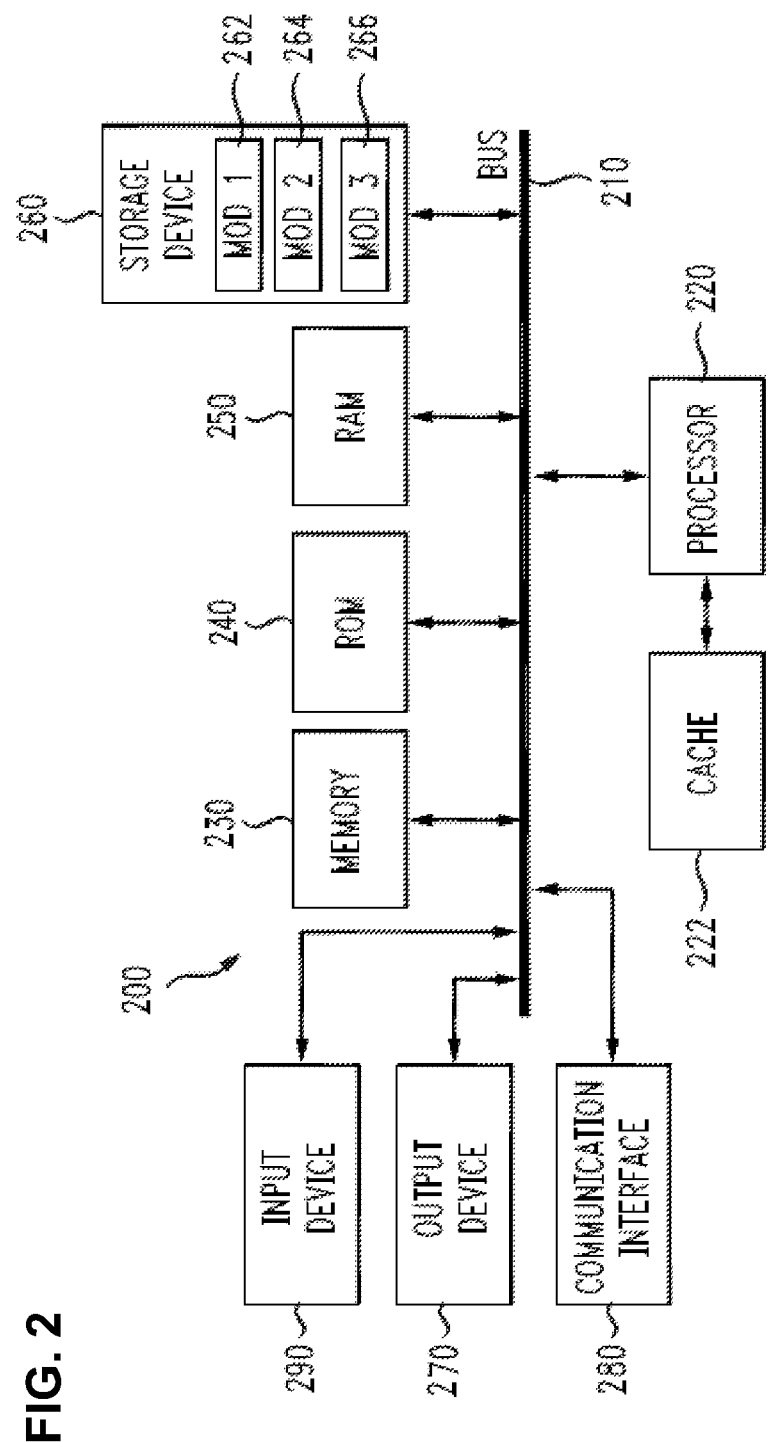
FIG. 2 is a schematic of an exemplary computing system for carrying out the various embodiments.

Having disclosed some basic concepts, the disclosure turns to the exemplary system and operating environment embodiments, and will then return to a discussion of registration according to the various embodiments disclosed herein. With reference to FIG. 2, an exemplary system 200 includes a general-purpose computing device 200, including a processing unit (CPU or processor) 220 and a system bus 210 that couples various system components including the system memory 230 such as read only memory (ROM) 240 and random access memory (RAM) 250 to the processor 220. The system 200 can include a cache 222 of high speed memory connected directly with, in close proximity to, or integrated as part of the processor 220. The system 200 copies data from the memory 230 and/or the storage device 260 to the cache 222 for quick access by the processor 220. In this way, the cache 222 provides a performance boost that avoids processor 220 delays while waiting for data. These and other modules can be configured to control the processor 220 to perform various actions. Other system memory 230 may be available for use as well. The memory 230 can include multiple different types of memory with different performance characteristics. It can be appreciated that the disclosure may operate on a computing device 200 with more than one processor 220 or on a group or cluster of computing devices networked together to provide greater processing capability. The processor 220 can include any general purpose processor and a hardware module or software module, such as module 2 262, module 2 264, and module 3 266 stored in storage device 260, configured to control the processor 220 as well as a special-purpose processor where software instructions are incorporated into the actual processor design. The processor 220 may essentially be a completely self-contained computing system, containing multiple cores or processors, a bus, memory controller, cache, etc. A multi-core processor may be symmetric or asymmetric.

The system bus 210 may be any of several types of bus structures including a memory bus or memory controller, a peripheral bus, and a local bus using any of a variety of bus architectures. A basic input/output (BIOS) stored in ROM 240 or the like, may provide the basic routine that helps to transfer information between elements within the computing device 200, such as during start-up. The computing device 200 further includes storage devices 260 such as a hard disk drive, a magnetic disk drive, an optical disk drive, tape drive or the like. The storage device 260 can include software modules 262, 264, 266 for controlling the processor 220. Other hardware or software modules are contemplated. The storage device 260 is connected to the system bus 210 by a drive interface. The drives and the associated computer readable storage media provide nonvolatile storage of computer readable instructions, data structures, program modules and other data for the computing device 200. In one aspect, a hardware module that performs a particular function includes the software component stored in a tangible and/or intangible computer-readable medium in connection with the necessary hardware components, such as the processor 220, bus 210, display 270, and so forth, to carry out the function. The basic components are known to those of skill in the art and appropriate variations are contemplated depending on the type of device, such as whether the device 200 is a small, handheld computing device, a desktop computer, or a computer server.

Although the exemplary embodiment described herein employs the hard disk 260, it should be appreciated by those skilled in the art that other types of computer readable media which can store data that are accessible by a computer, such as magnetic cassettes, flash memory cards, digital versatile disks, cartridges, random access memories (RAMs) 250, read only memory (ROM) 240, a cable or wireless signal containing a bit stream and the like, may also be used in the exemplary operating environment. Tangible, non-transitory computer-readable storage media expressly exclude media such as energy, carrier signals, electromagnetic waves, and signals per se.

To enable user interaction with the computing device 200, an input device 290 represents any number of input mechanisms, such as a microphone for speech, a touch-sensitive screen for gesture or graphical input, keyboard, mouse, motion input, speech and so forth. An output device 270 can also be one or more of a number of output mechanisms known to those of skill in the art. In some instances, multimodal systems enable a user to provide multiple types of input to communicate with the computing device 200. The communications interface 280 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 220. The functions these blocks represent may be provided through the use of either shared or dedicated hardware, including, but not limited to, hardware capable of executing software and hardware, such as a processor 220, that is purpose-built to operate as an equivalent to software executing on a general purpose processor. For example the functions of one or more processors presented in FIG. 2 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 240 for storing software performing the operations discussed below, and random access memory (RAM) 250 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 200 shown in FIG. 2 can practice all or part of the recited methods, can be a part of the recited systems, and/or can operate according to instructions in the recited tangible computer-readable storage media. Such logical operations can be implemented as modules configured to control the processor 220 to perform particular functions according to the programming of the module. For example, FIG. 2 illustrates three modules Mod1 262, Mod2 264 and Mod3 266 which are modules configured to control the processor 220. These modules may be stored on the storage device 260 and loaded into RAM 250 or memory 230 at runtime or may be stored as would be known in the art in other computer-readable memory locations.

Figure 3:
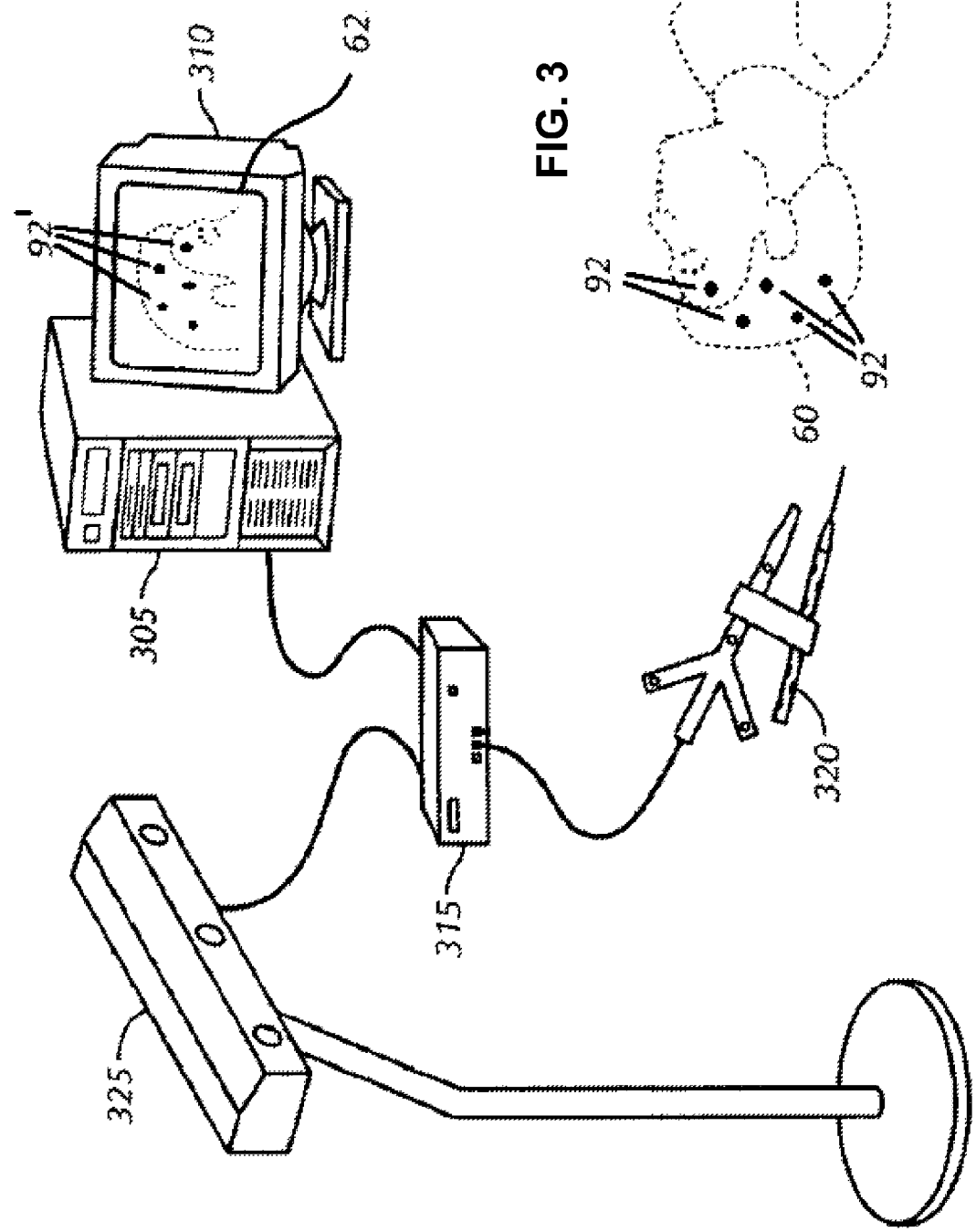
FIG. 3, is a schematic of an exemplary environment in which the various embodiments can be used.

FIG. 3 shows an exemplary image-guided surgical system 300 that can be used with the various embodiments. The image-guided surgical system 300 can include a computer (an image data processor) 305 with memory and a display monitor 310. For example, computer 300 can be configured with accordance with the computing device of FIG. 2. A high-speed interface in the computer 305 communicates with a surgical probe/instrument 320 via control box 315, although the features of the control box 315 could be incorporated directly into the computer 305. The surgical probe/instrument 320 may be an investigatory probe, an electro surgical stimulation device, a coagulation device, an ablation device, a drill, a laser and the like, as is known in the art. Additionally, the system can include an optical tracking sensor 325 configured for tracking the location of reference emitters or markers 92 on a patient 60.

One exemplary tracking sensor 325 for use with the image-guided surgical system 300 is the Optotrak 3020 commercially available from Northern Digital Inc., Waterloo, Ontario, Canada. The optical tracking sensor 325 contains three cylindrical lenses which receive light from sequentially strobed infrared light-emitting diodes (IREDs). Triangulation is used to find each IRED relative to the position of the optical tracking sensor 325. Typical image-guided surgery tracking systems which utilize an optical tracking sensor are described in U.S. Pat. No. 6,584,33 B2.

While the exemplary image-guided surgical system 300 tracks optically using IREDs and an optical tracking sensor technology, other similar tracking technologies can be utilized without departing from the present invention. For example, the image-guided surgical system 300 can use a plurality of cameras (not shown) linked to the computer 305 or control box 315 which detect geometric patterns. An example system is the MicronTracker commercially available from Claron Technology, Toronto, Ontario, Canada. Other tracking technologies may include electromagnetic tracking, passive binocular cameras, smart-transmitters/emitters and the like.

In order for the position and orientation of the surgical probe/instrument 320 to be measured by the optical tracking sensor 325, the surgical probe/instrument 320 can includes a handle with multiple IREDs distributed over the surface of a handle of the surgical probe/instrument 320 so that at least three IREDs are visible in all of the appropriate orientations of the surgical probe/instrument 320. If three or more IREDs attached to the handle of the surgical probe/instrument 320 are detected by the lenses of the optical tracking sensor 325, the tip of the surgical probe/instrument 320 can be accurately localized in physical space without placing constraints on how the surgical probe/instrument 320 needs to be handled by a user (e.g., a technician, nurse, surgeon or the like), The optical tracking sensor 325 can localize both the surgical probe/instrument 320 and the markers 92 in sensor unit space.

Based on the information from sensor 325 and image data 62 of the patient indicating a position and orientation of the markers 92 in the image space (92'), the computer 305 can be used by the user to correctly place the instrument 320 in the physical space or determine a position of the instrument 320 relative to a feature or structure of interest in patient 60 and shown in patient image 63.

The configuration above is presented solely for illustratively purposes and the various embodiments are not limited in this regard. Rather, the various embodiments can be used for any other type of computer-guided or computer-assisted tracking, processes, and/or procedures.

Figure 4:
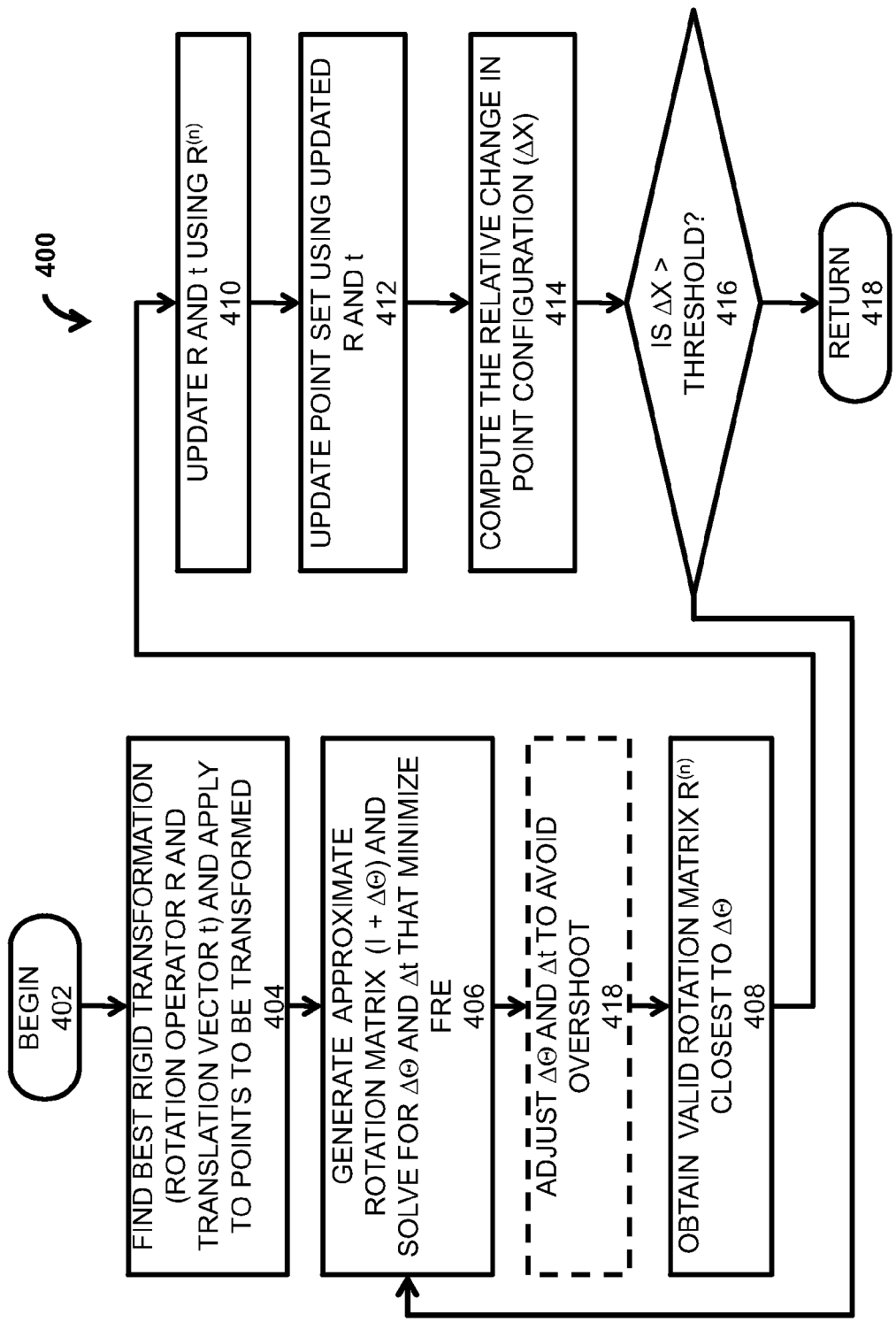
FIG. 4 is a flowchart of steps in an exemplary method for performing registration in accordance with the various embodiments.

Having described exemplary systems and environments for the various embodiments, the disclosure now turns to FIG. 4. FIG. 4 is a flowchart of steps in an exemplary method 400 for providing a point-based rigid registration between N three-dimensional points in two spaces, where N is an integer greater than 2. In particular, method 400 is configured to determine the transformation that minimizes the anisotropically weighted fiducial registration error (FRE), which is square root of the mean of the sum of squares of weighted individual fiducial registration errors. In the various embodiments, $X=\{x_i\}$, $i=1 \ldots N$ is the set of 3-by-1 fiducial points to be transformed (e.g., from image space), hereinafter called the "moving" fiducials, and $Y=\{y_i\}$, $i=1 \ldots N$ is the fiducial points to which they are to be registered (e.g., in physical space), hereinafter called the "stationary" fiducials. The goal is to find the 3-by-3 rotation matrix R and 3-by-1 translation vector t that minimize:

$$FRE^2 = \frac{1}{N}\sum_{i=1}^{N} |W_i(Rx_i + t - y_i)|^2, \quad (1)$$

where $W_i$ is a 3-by-3 matrix of weights for fiducial i. However, the problem is made difficult by the nonlinear constraint on the rotation matrix, namely, $R^1R=I$, where I is the identity.

The weights account for variation in the localization accuracy among the fiducials, a variation with respect to direction and with respect to the fiducials. For purpose of the disclosure, the former variation is referred to as "anisotropy" and the latter variation is referred to as "inhomogeneity". If $W_i=W_j$ for all i,j, then FLE is homogeneous. In the various embodiments, it is assumed that FLE for each fiducial is normally distributed with zero mean and can be resolved into three uncorrelated components along a set of orthogonal principal axes, with standard deviations $\sigma_{i\alpha}$, $\alpha=1, 2, 3$. Thus, if $\sigma_{i\alpha}=\sigma_{i\beta}$, the problem reduces to the isotropic problem, which is easily solved by closed-form methods, both for the homogenous and the inhomogeneous cases.

For many tracking systems, the distance from the camera or sensor to the fiducials is much larger than distances between fiducials, in this case, the principle axes are approximately the same for all fiducials. Thus, $V_i \approx V$. With that assumption, without loss of generality, one can assume that $V=I$. Thus, the reorienting of the coordinate system to that of the camera can be accomplished, which results in the replacement of each $x_i$ with $Vx_i$ and each $y_i$ with $Vy_i$.

The various embodiments provide a method that is iterative, where the strategy is to replace, at each iterative step, the exact, nonlinear problem with a simple, linear problem, which can be solved exactly by linear algebra. The simplification involves replacing the rotation matrix by an approximating to the rotation matrix that is subject only to a linear constraint, Thus, the exact solution to the linear algebra problem gives an approximate solution to the registration problem. However, the approximate matrix is then replaced with the rotation matrix that is closest in the least-squares sense to the approximate matrix, and that rotation matrix is then applied to the moving fiducials to bring them incrementally closer to the stationary fiducials.

In summary, the method provides for repeatedly (1) Solving the linearized problem, (2) finding the closest rigid transformation to the linear solution, and (3) applying the rigid transformation to the moving fiducials, stopping when the fiducial movement is below threshold.

Referring now to FIG. 4, method 400 begins at step 402 and proceeds to step 404. Normally, at each stage of the iteration a set of points is transformed to a new set of points. That is, at iteration stage n, the points $x_i^{(n-1)}$ are transformed to the points $x_i^{(n)}$. However, at step 404, before the iterations begin, an initialization is performed by solving Eq. (1) for isotropic, homogeneous FLE, i.e. omitting $W_i$. That is, at step 404, the best rigid transformation based on isotropic FLE is obtained and applied to the point to be transformed. In one embodiment, the solution is effected by means of the closed-form solution given by Algorithm 8.1 described by J. M. Fitzpatrick et al. in "Registration", Medical Image Processing, Volume II of the Handbook of Medical Imaging, M. Sonka and J. M. Fitzpatrick, ed., SPIE Press (2000), the contents of which are hereby incorporated in their entirety. The resulting rotation matrix and translation vector calculated. The rotation and translation of the solution are then initialized as $R=R^{(0)}$ and $t=t^{(0)}$. After the initialization at step 404, each stage n of the iteration comprises the steps described below.

First, at step 406, an approximation of Eq. (1) is solved. In particular, $x_i$ is replaced by $x_i^{(n-1)}$ and R is replaced by an approximate rotation matrix, $I+\Delta\Theta$, where $\Delta\Theta^t=-\Delta\Theta$, which is equivalent to the linear constraint, $(R-I)=-(R-I)^t$. This approximate rotation matrix is also referred to as a "linearized matrix" because the nonlinear constraint $R^tR=I$ that defines a rotation matrix has been replaced by the linear constraint. Conceptually, this involves approximating R based on the following assumptions when $\theta$ is small: (1) $\cos\theta$ is approximately equal to 1; (2) $\sin\theta$ is approximately equal to $\theta$, and (3) $\theta_\alpha\theta_\beta$ is approximately equal to 0. Such an assumption can be made since at step 404, since the points are transformed by the best rigid transformation based on isotropic FLE. Thus, the angles in the rotation operation for the transformed points are reduced to small values for which the listed assumptions apply. Following this simplification, the following approximation of Eq. (1) can then be minimized:

$$FRE^2 = \quad (2)$$
$$\frac{1}{N}\sum_{i=1}^{N}((I+\Delta\Theta^{(n)})x_i^{(n-1)} + \Delta t^{(n)} - y_i)^t W_i^2 ((I+\Delta\Theta^{(n)})x_i^{(n-1)} + \Delta t^{(n)} - y_i)$$

The $\Delta\Theta^{(n)}$ and translation vector, $\Delta t$, that together minimize Eq. (2), can be found exactly, as described in greater detail below.

Once the $\Delta\Theta^{(n)}$ and translation vector, $\Delta t^{(n)}$ that minimize Eq. (3) have been found at step 406, the method 400 proceeds to step 408. It is worth noting that the linearized matrix obtained at step 406 cannot be utilized as a rotation matrix for the transformation. Accordingly, at step 408, a rotation matrix $R^{(n)}$ is obtained based on the $\Delta\Theta$ obtained at step 406. Specifically, $R^{(n)}$ is selected such that $R^{(n)}$ is closest in the least-squares sense to $\Delta\Theta$ In particular, a singular value decomposition (SVD) of $\Delta\Theta$ is obtained ($U\Lambda V^t=\Delta\Theta$, where U and V are rotation matrices and $\Lambda$ is a diagonal matrix with non-negative elements). Thereafter, the rotation matrix is obtained by using $R^{(n)}=UV$. (As is shown in greater detail below, this matrix is the proper rotation matrix that is closest in the least-squares sense to $\Delta\Theta$.)

After a rotation matrix is obtained at step 408, an updated rotation matrix and translation vector can be obtained at step 410. In particular, an updated rotation matrix is calculated using $R=R^{(n)}R$. Similarly, an updated translation vector is calculated: $t=R^{(n)}t+\Delta t^{(n)}$. Thereafter, an updated point set is calculated at step 412 using: $x_i^{(n)}=Rx_i+t$ for $i=1, \ldots, N$.

Following step 412, the relative change in the configuration of the points can be calculated at step 414 as $\Delta X^2 = \sum_{i=1}^{N} |x_i^{(n)}-x_i^{(n-1)}|^2 / \sum_{i=1}^{N} |x_i^{(n)}-\overline{x}^{(n)}|^2$ where is the centroid of the point configuration $\{x_i^{(n)}\}$. Thereafter $\Delta X$ is compared to a threshold $\tau$ at step 416. If $\Delta X > \tau$ at step 416, n is set equal to n+1 and the method proceeds to step 406 to perform another iteration. Otherwise, the method 400 ends at step 418 and resumes previous processing.

In some cases, it is possible $\Delta X$ will never be tower than the threshold. That is, the transformations generated by method 400 can result in an "overshoot" of the points during each iteration, thus resulting a non-converging condition. Accordingly, in some embodiments, method 400 can include an additional step 420 to be performed after at least one iteration has been completed and after step 406. In particular, to prevent overshoot of the points, $\Delta\Theta$ and $\Delta t$ are adjusted to prevent overshoot. In one embodiment, the amount of adjustment of the translation is reduced based on the calculated $\Delta\Theta$ and $\Delta t$ during a current and prior iteration. For example, $\Delta\Theta$ and $\Delta t$ can be adjusted so that $\Delta\Theta=(\Delta\Theta^{(n-1)}+\Delta\Theta^{(n)})/2$ and $\Delta t=(\Delta t^{(n-1)}+\Delta t^{(n)})/2$. As a result, the likelihood of convergence is increased.

As noted in step 406, method 400 begins each iteration by finding $\Delta\Theta^{(n)}$ and $\Delta t^{(n)}$ that minimize the expression for $FRE^2$ in Eq. (2). This minimization is equivalent to finding the least-squares solution to the set of 3N equations:

$$W_i \Delta\Theta^{(n)} x_i^{(n-1)} + W_i \Delta t^{(n)} = W_i \Delta_i^{(n-1)}, \quad (3)$$

where $\Delta_i^{(n-1)} = y_i - x_i^{(n-1)}$. The unknowns in these equations are the six nonzero elements of the 3-by-3 anti-symmetric matrix $\Delta\Theta^{(n)}$ and the three elements of the vector $\Delta t^{(n)}$. For an anti-symmetric matrix the diagonal elements all equal zero and among the off-diagonal elements $\Delta\Theta_{ij}^{(n)} = -\Delta\Theta_{ji}^{(n)}$. As a result of these restrictions, there are only three independent unknowns in $\Delta\Theta^{(n)}$: namely, $\Delta\Theta_{32}^{(n)}$, $\Delta\Theta_{13}^{(n)}$, and $\Delta\Theta_{21}^{(n)}$.

The meaning of these three elements can be understood by recalling that $I+\Delta\Theta^{(n)}$ is an approximation of a rotation R, as discussed with respect to step 406 above. If the angle of rotation of R about its axis is small, then the movement, $Rx_i^{(n)} - x_i^{(n)}$, can be approximated as a cross product between the axis of rotation of R and the vector $x_i^{(n)}$. If the vector $\Delta\theta$, whose elements are $\Delta\theta_1 = \Delta\Theta_{32}^{(n)}$, $\Delta\Theta_{13}^{(n)}$, and $\Delta\Theta_{21}^{(n)}$, is provided, then for small rotations, the axis of rotation lies approximately along $\Delta\theta$, and the angle of rotation is approximately equal to the length of $\Delta\theta$, and $$Rx_i^{(n)} - x_i^{(n)} \approx \Delta\theta \times x_i^{(n)}. \quad (4)$$

$\Delta\theta$ can then be used transform Eqs. (3) into the canonical form $$Cq=e, \quad (5)$$

where C is a 3N-by-6 matrix, q is a 6-by-1 vector of unknowns, and e is a 3N-by-1 column vector. The elements of q are as follows:

$$q_1=\Delta\theta_1, q_2=\Delta\theta_2, q_3=\Delta\theta_3, q_4=\Delta t_1, q_5=\Delta t_2, q_6=\Delta t_3. \quad (6)$$

To give the elements of C and e, the jk element of $W_i$ needs to specified. This can be denoted using $W_{jk,i}$, where the third subscript is separated by a comma to emphasize that it is not a matrix index, but a fiducial index. Additionally, element j of $\Delta_i^{(n)}$ also needs to specified, which can be denoted with two subscripts: $\Delta_{j,i}^{(n)}$, here separating the second subscript with a comma to emphasize that it is not a vector index, but a fiducial index. With this notation established, one can find, by means of a detailed inspection of Eq. (3), that $$C_{3(i-1)+j,1} = -W_{j2,i}x_{3i}^{(n)} + W_{j3,i}x_{2i}^{(n)},$$

$$C_{3(i-1)+j,2} = +W_{j1,i}x_{3i}^{(n)} - W_{j3,i}x_{1i}^{(n)},$$

$$C_{3(i-1)+j,3} = -W_{j1,i}x_{2i}^{(n)} + W_{j2,i}x_{1i}^{(n)},$$

$$C_{3(i-1)+j,4} = W_{j1,i},$$

$$C_{3(i-1)+j,5} = W_{j2,i},$$

$$C_{3(i-1)+j,6} = W_{j3,i}, \quad (7)$$

and $$e_{3(i-1)+j,1} = W_{j1,i}\Delta_{1,i}^{(n)} + W_{j2,i}\Delta_{2,i}^{(n)} + W_{j3,i}\Delta_{3,i}^{(n)}. \quad (8)$$

With these definitions, the solution to Eq. (2) is found by solving Eq. (5) for q by using any appropriate numerical method, and then setting $$\Delta\Theta = \begin{bmatrix} 0 & -q_3 & q_2 \\ q_3 & 0 & -q_1 \\ -q_2 & q_1 & 0 \end{bmatrix} \quad (9)$$

and $$\Delta t = [q_4 \quad q_5 \quad q_6]^t. \quad (10)$$

Any appropriate numerical method may be employed to solve Eq. (5), such as the pseudo-inverse or singular-value decomposition of C.

As described above with respect to step 408, a rotation matrix R(n) closest to $\Delta\Theta$ is obtained via use of SVD method. In particular, at step 408, $R^{(n)}UV^t$, where U and V are rotation matrices obtained from the singular value decomposition of the approximate rotation matrix: $U\Lambda V^t = I + \Delta\Theta$. It can be proved that $R^{(n)}$ found in Step 3 of our iterative algorithm is the closest rotation matrix to $I+\Delta\Theta$ in the least squares sense as follows. First, let $M=I+\Delta\Theta$ and let R be the closest rotation matrix to M which defines a difference $E=M-R$. Thus, if $|E|^2$ is equal the sum of squares of the elements of E, then:

$$|E|^2 = \sum_{i,j}(M_{ij} - R_{ij})^2 \quad (11)$$

$$= \text{trace}(M-R)^t(M-R)$$

$$= \text{trace } M^tM - 2 \text{ trace}(M^tR) + \text{trace}(I).$$

For purposes of Eq. (12), the R of interest is the one that minimizes $|E|^2$. From the last line of Eq. (11), one can see that $|E|^2$ is minimized when trace $(M^tR)$ is maximized. To maximize this trace, the SVD of M is employed: $U\Lambda V^t = M$, where U and V are rotation matrices and $\Lambda$ is diagonal and has nonnegative elements. Using this formulation for M in trace $(M^tR)$, this provides:

$$\text{trace}(M^tR) = \text{trace}(V\Lambda U^tR) \quad (12)$$

$$= \text{trace}(\Lambda U^tRV)$$

$$= \text{trace}(\Lambda Z)$$

$$= \sum_{i=1}^{3} \Lambda_{ii}Z_{ii},$$

where $Z=U^t RV$. It is worth noting that, by virtue of its being a product of rotation matrices, Z is also a rotation matrix. The maximum value for any element of a rotation matrix is 1. Since each $\Lambda_{ii}$ is nonnegative, the maximum of the sum in the last line of Eq. (12) is reached when $Z_{ii}=1$ for i=1, 2, 3. Thus, Z is the 3-by-3 identity matrix I. Therefore, $I=U^t RV$. By multiplying this equation on the left by U and on the right by $V^t$, we find that $R=UV^t$, which completes the proof.

Further, R can be shown to be proper as follows. A proper rotation matrix has a nonnegative determinant. Thus, it is necessary to show that the determinant of R is nonnegative. As one of ordinary skill in the art will recognize, for all products AB, det(AB)=det(A)det(B). Accordingly, $$\det(I + \Delta\Theta) = \det(U)\det(\Lambda)\det(V^t) \qquad (13)$$
$$= \det(\Lambda)\det(UV^t)$$
$$= \det(\Lambda)\det(R).$$

Further, since the determinant of a diagonal is the product of its diagonal elements, all of which are nonnegative for $\Lambda$ by virtue of the properties of singular value decomposition, the sign of the determinant R is equal to the sign of $\det(I+\Delta\Theta)$. The expression for this latter determinant can be found directly as:

$$\det(I + \Delta\Theta) = \det\begin{bmatrix} 1 & -\Delta\theta_3 & \Delta\theta_2 \\ \Delta\theta_3 & 1 & -\Delta\theta_1 \\ -\Delta\theta_2 & \Delta\theta_1 & 1 \end{bmatrix} \qquad (14)$$
$$= 1 + \Delta\theta_1^2 + \Delta\theta_2^2 + \Delta\theta_3^2,$$

which is nonnegative. Thus, the determinant of R is also nonnegative, which completes the proof.

As noted above, each fiducial i is associated with a weight matrix $W_i$, which is a 3-by-3 matrix of weights. In the various embodiments, the weights can be computed in a variety of ways. However, the various embodiments are not limited solely to the methods described below and any other suitable methods for calculating the weights can be used as well.

In one exemplary method for computing weights, which is appropriate when the weighting is homogeneous (i.e., $W_i$ is the same for each fiducial) so that $W_i=W$, the weighting can determined using the FLE estimates from the algorithm proposed by Wiles and Peters in "Real-time estimation of FLE statistics for 3D tracking with point-based registration", IEEE Transactions on Medical Imaging 28(9) (September 2009) 1384-1398, the contents of which are herein incorporated in their entirety. In this method, the FLE covariance matrix can then be found by solving a set of linear equations that relates the FLE statistics to the estimated FRE statistics: $A_\alpha x_\alpha = b_\alpha$ where $A_\alpha$ is based on the geometry of the tracked rigid body, each element of $x_\alpha$ is one of the six independent FLE covariance components and each element of $b_\alpha$ is one of the six independent fiducial registration error (FRE) components estimated from the previous M frames. For an optical tool with N tracked fiducial markers, there are N sets of linear equations that can be solved in order to obtain an estimate of the FLE covariance matrix. However, to improve numerical stability we can solve an over-determined set of equations by stacking the matrices and vectors such that:

$$x_{avg} = (A_{stack}^t A_{stack})^{-1} A_{stack}^t b_{stack}. \qquad (16)$$

where $$A_{stack} = \begin{bmatrix} A_1 \\ A_2 \\ \vdots \\ A_N \end{bmatrix} \text{ and } b_{stack} = \begin{bmatrix} b_1 \\ b_2 \\ \vdots \\ b_N \end{bmatrix}. \qquad (17)$$

Taking the six independent FLE covariance components from $x_{avg}$ (with or without stacking) and rewriting them as the FLE covariance matrix $\Sigma$, the weighting matrix is computed as $$W = \Sigma^{-1/2}. \qquad (18)$$

In another embodiment, the weights can be computed to deal with the scenario in which the localization errors is inhomogeneous and anisotropic it both spaces. This is the situation that arises in surgical navigation when the localization error of the physical tracking system in the operating room suffers from a relatively larger standard deviation in the direction from the camera to the fiducial than in the perpendicular directions and the slice thickness is in the pre-operative image is not much larger than the smallest dimension of the fiducial markers. As a result, the weighting matrix has the form $$W_i = (RV_{xi}\text{diag}(\sigma_{xi1}^2, \sigma_{xi2}^2, \sigma_{xi3}^2)V_{xi}^{-1}R^1 + V_{yi}\text{diag}(\sigma_{yi1}^2, \sigma_{yi2}^2, \sigma_{yi3}^2)V_{yi}^t)^{-1/2}, \qquad (19)$$

where $V_{\alpha i}{}^t V_{\alpha i}=I$, $\alpha=x, y$, where I is the 3×3 identity matrix, and x and y denote the x-space and the y-space. The columns of are the principal axes of the FLE for fiducial i in space $\alpha$. Accordingly, an "ideal" weighting is provided by deriving the information regarding the weighting from the anisotropic FLE. This calculation of $W_i$ is carried out at Step 406 (FIG. 4), so that $W_i$ can be used in Eq. (3).

In still another embodiment, a general weighting can be provided means of a specific two-space weighting scheme. That is, the weighting need not be derived from information known about the anisotropic FLE.

In general, "weighting", as used herein, refers to the multiplication of the fiducial registration error vector for each point pair by a matrix. The point pair consists of a point in the X space and a point in the Y space which are to be aligned. The points in X space have been transformed by a rigid transformation in an effort to align them, or "register" them, with their corresponding points the Y space. The alignment error, or "fiducial registration error", for a given point pair is the difference between the position of the transformed X point and its corresponding Y point. Because each position is represented by a vector, the difference between them is also a vector. This weighting is referred to as "two-space" weighting because the weighting is applied to a vector derived from points in two spaces. In such embodiments, the two-space weighting matrix must be updated by recalculation at each step in the algorithm.

Typically, the motivation for weighting is to give more or less influence to the components of fiducial registration error. The weighting may vary from point pair to point pair and from x direction to y direction to z direction. Such variation in influence can be accomplished by multiplying the fiducial registration error by a diagonal matrix, but multiplication by a matrix that is not diagonal can also rotate the vector, which means that, even if the x component of the unweighted vector is zero, the x component of the weighted vector may be non-zero. Both general and ideal weighting allow for both diagonal and non-diagonal matrices, and thus both allow for rotation. Thus whether the weighting matrix is diagonal or not does not distinguish between general and ideal weighting.

Weighting is typically specified by the user by providing one matrix each for the points in the X space and one matrix each for points in the Y space. For each pair of corresponding points, i.e., one in the X space and one in the Y space, their two matrices must be combined into a single two-space weighting matrix. That two-space weighting matrix must be recalculated at each step of the iteration for each pair of points.

The ideal weighting scheme is a calculation of the two-space weighting matrix at each step of the algorithm based on the statistics of the anisotropic fiducial localization error. Those statistics comprise the spatial covariance of fiducial localization error for each point. The spatial covariance for Point i in space X is a 3-by-3 matrix $S_{xi}$ and for Point i in space Y is a 3-by-3 matrix $S_{yi}$. For ideal weighting, the two-space weighting matrix $W_i$ for point i is calculated from the two matrices, $S_{xi}$ and $S_{yi}$ as follows:

$$W_i = (RS_{xi}R^t + S_{yi})^{-1/2} \quad (20)$$

As described above with respect to Eq. (19). As with Eq. (19), this calculation of W is carried out at Step 406 (FIG. 4), so that $W_i$ can be used in Eq. (3).

In contrast, the general weighting scheme e in accordance with the various embodiments of the invention is based on the user's specification of a "one-space" weighting matrix, instead of a covariance matrix, for each point in each space. Thus, with general weighting, the user specifies a 3-by-3 weighting matrix $W_{xi}$ for Point i in space X and a 3-by-3 weighting matrix $W_{yi}$ for Point i in space Y. These matrices may be determined empirically without direct knowledge of the statistics of the fiducial localization error. Accordingly, for general weighting, the two-space weighting matrix $W_i$ is calculated as follows:

$$W_i = (R(W_{xi}^t W_{xi})^{-1} R^t + (W_{yi}^t W_{yi})^{-1})^{-1/2} \quad (21)$$

It should be noted that, as long as each $W_{xi}$ and $W_{yi}$ are of rank 3, it is assured that the inverse square root exists and that it is real. If the user wishes to specify a zero weight for one or two directions for one or both spaces, one or both of $W_{xi}$ and $W_{yi}$ may have rank less than 3. However, for all practical situations this problem can be solved by replacing the zero weight with a negligible but finite weight. Thus, for general weighting $W_i$ exists and is real for all practical problems. As with Eqs. (19) and (20), this calculation of $W_i$ is carried out at Step 406 (FIG. 4), so that $W_i$ can be used in Eq. (3).

Typically the user provides one-space matrices that are symmetrical. Therefore, typically $W_{xi}^1 W_{xi} = W_{xi}^2$ and $W_{yi}^1 W_{yi} = W_{yi}^2$.

General weighting described above is useful when the covariances are not known and the user instead must choose point weightings heuristically based on partial knowledge of the fiducial localization error. For example, if for Point i, the user has low confidence in one spatial direction of localization in space X, the weighting in that direction should be low in $W_{xi}$. Similarly, if there is high confidence in one spatial direction of localization in space Y, the weighting in that direction should be high. The general weighting scheme described herein shows how these heuristically determined point weightings should be combined into a two-space weighting for Point i.

Further, the general form can also be reduced to the ideal weighting or adapted to specify any other weighting scheme. In the case of ideal weighting, a user would calculate the two one-space weighting matrices for Point i as $W_{xi} = S_{xi}^{-1/2}$ and $W_{yi} = S_{yi}^{-1/2}$. It should be noted that as long as there is non-zero localization in all spatial directions, the covariances are of rank 3 and are in fact positive definite. As a result, it is assured that the inverse square roots exist, are of rank 3, and are real, Thus, both $W_{xi}$ and $W_{yi}$ exist, are of rank 3, and are real. Therefore, when such general weighting used to implement ideal weighting in the various embodiments, $W_i$ exists and is real.

EXAMPLES

Having disclosed the general operation of the various embodiments, the disclosure now turns to several examples of registration processes in accordance with the various embodiments. These examples are not intended to be limiting, but rather are shown here to illustrate the various advantages and benefits of the various embodiments.

A first registration process in accordance with the various embodiments was tested in conjunction with a tracking methodology for use with a handheld tool and for a robotic application, where the weightings were based on Wiles and Peters method described above. For purposes of this test, two tracked rigid bodies where provided. A first set of four markers were provided, representing tracking markings rigidly attached to a tool, and a second set of four markers, representing the target. The second set of markers were arranged so that, for the robotic application, the centroid is at the tip of the drill and for the hand-held-tool application the centroid is at the tip of the probe pointer. Previous to the tracking experiments, a standard 'tool definition' calibration was carried out. The robotic arm was held stationary in several poses while the positions of the tool markers and the target markers were measured repeatedly (1.000 s of times). The average of these measurements over the various poses for each marker provides a highly accurate standard configuration. The centroid of the four markers on the right is defined to be the 'target' position (e.g., drill tip, or probe pointer tip). Then, during the tracking experiments, each detected configuration of the tool is registered to the standard tool. Therefore, using the right-hand rigid body to estimate the true location of the target, the target is estimated with target localization error (TLE) statistics of:

$$\Sigma_{tle} = \frac{\Sigma_{fle,1} + \Sigma_{fle,2} + \ldots + \Sigma_{fle,N}}{N^2}, \quad RMS_{tle} = \sqrt{\text{trace}(\Sigma_{tle})} \quad (22)$$

where N is the number of markers on a tool (N=4 for our example) and RMS is the root-mean-square statistic. If the FLE is homogeneous across the markers, then the covariance matrix and RMS reduce to $\Sigma_{tle} = \Sigma_{fle}/N$ and $RMS_{tle=RMSfle}/\sqrt{N}$, respectively.

The total registration error (TRE) statistics of the isotropic and anisotropic registrations algorithms were then compared using the centroid of the right-hand tracked tool as the target ground truth. The two rigid bodies are rigidly attached to one another and moved together. The following experimental protocol was used to carry out these steps for every frame of data returned from ate tracking system:

(i) The 3D positions of each of the markers on both rigid bodies are measured with the optical tracking system at an instance in time which we will refer to as a frame of data.

(ii) The target location, $r_{ref}$ is obtained by taking the mean of the four markers on the right-hand tracked tool.

(iii) The right-hand tracked tool is registered using isotropic registration and the FLE estimates are updated for these markers. The TLE statistics of the target are obtained using Eq. (22).

(iv) The left-hand tracked tool is registered using isotropic registration and the FLE estimates are updated for these markers. The target location, $r_{iso}$, was computed using the transform computed from isotropic registration.

(v) The left-hand tracked tool is registered using anisotropic registration using the FLE estimates of the markers for the weighting as per (3). The target location, $r_{aniso}$ is computed using the transform computed from anisotropic registration.

(vi) The TRE vectors for both registration methods are computed such that $tre_{iso} = r_{iso} - r_{ref}$ and $tre_{aniso} = r_{aniso} - r_{ref}$.

After 1000 frames of data are collected, the results were plotted and a set of observational statistics were computed. Using ate methodology described above, a tracking method relying on anisotropic registration was compared to with traditional tracking methods using isotropic registration. The tracked tools were placed at a distance of approximately 160 cm from the tracking system. Data was collected under the following conditions:

Test A: translate approximately 10 cm parallel to Polaris' x-axis (up{down)

Test B: translate approximately 10 cm parallel to Polaris' y-axis (left{right)

Test C: translate approximately 10 cm parallel to Polaris' z-axis (front{back)

Test D: translate in all directions

Test E: rotate in all directions

Test F: random path including translations and rotations

A total of 1000 frames of data was collected for each test. Since a sliding window of 200 frames was used to estimate the FLE, only the last 800 frames are used for statistical analysis because it takes 200 frames until the FLE estimate stabilizes.

Three key sets of results are presented in Table 1, as shown below, First, an estimate of the TLE RMS is given using Eq. (22) with estimates of the FLE covariance matrices found from the same FLE estimation algorithm used to determine the weightings for the anisotropic registration algorithm.

TABLE 1

Results of Tests A-F

| Test | TLE RMS | TRE RMS Isotropic | TRE RMS Anisotropic | TRE RMS % Diff. | TRE RMS % Diff Corr. |
|---|---|---|---|---|---|
| A | 0.08 mm | 0.22 mm | 0.18 mm | −19.3% | −22.6% |
| B | 0.07 mm | 0.33 mm | 0.19 mm | −42.4% | −45.2% |
| C | 0.08 mm | 0.32 mm | 0.18 mm | −42.8% | −46.8% |
| D | 0.06 mm | 0.34 mm | 0.24 mm | −28.7% | −29.9% |
| E | 0.08 mm | 0.60 mm | 0.46 mm | −23.2% | −23.7% |
| F | 0.06 mm | 0.34 mm | 0.22 mm | −34.5% | −36.0% |

For Table 1, all statistics are computed over the usable 800 frames. The estimate of the TLE RMS is provided using Eq. (22). The TRE RMS statistics are computed for all the distance errors in a given test. The percent difference between the two methods is shown using the the isotropic RMS as the reference. Finally, noting that the TLE contributes to the measured TRE RMS statistic, the TRE RMS statistics were corrected and the TRE RMS difference was recomputed.

Next, the TRE RMS computed for both the isotropic and anisotropic registrations are provided. It is worth noting that the anistropic TRE RMS is lower for each test and the percent difference between the two statistics is provided. The percent difference is computed using the isotropic registration as the reference value so that:

$$\% \text{ Diff} = 100 \times (RMS_{tre,aniso} - RMS_{tre,iso})/RMS_{tre,iso}. \quad (23)$$

Additionally, the TRE RMS for each registration has a contribution from the TLE where the measured TRE RMS can be related to the actual TRE RMS by:

$$RMS_{tre,meas}^2 = RMS_{tre,actual}^2 + RMS_{tle}^2. \quad (24)$$

Taking into consideration this relationship, the percent differences between isotropic and anisotropic TRE RMS statistics can be corrected by using the $RMS_{tre,actual}$ and show this new percent difference in the last column of Table 1. A small increase in the accuracy is observed with this correction.

Figure 5:
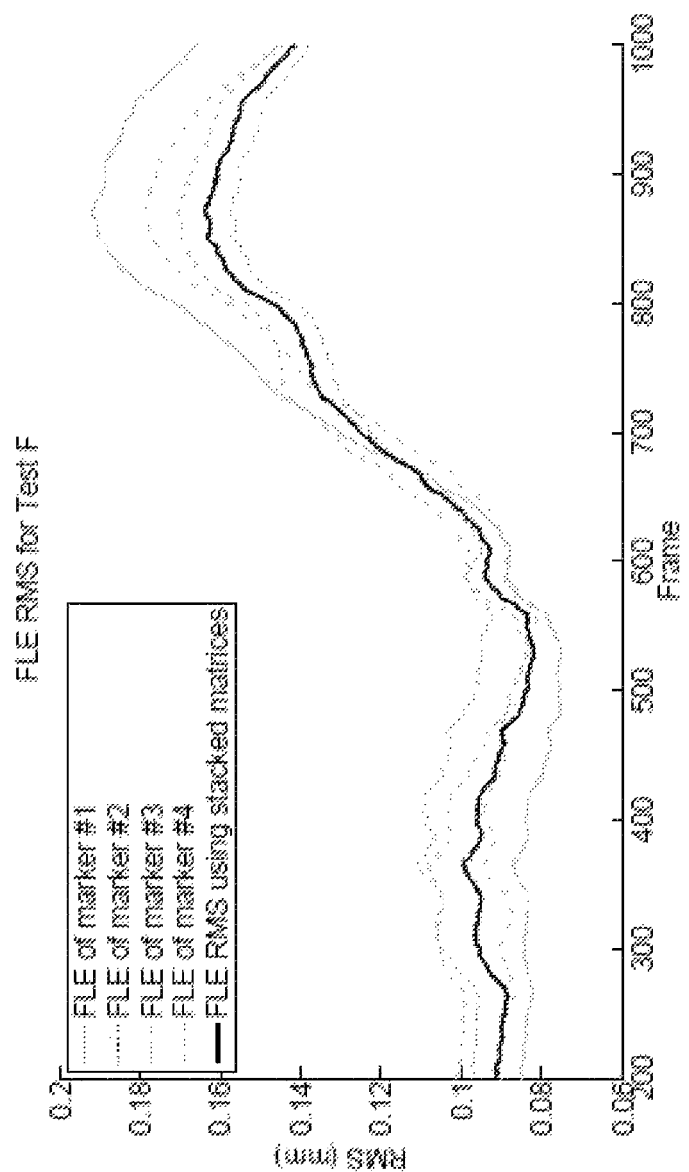
FIG. 5 is an x-y plot showing FLE RMS results for a tracking process using a registration method in accordance with an embodiment.

Moving beyond the observational statistics, we provide details of the data measured during Test F. In FIG. 5, the FLE RMS estimates are provided for (i) each marker estimated individually and (ii) the average FLE estimated by solving the over-determined system of equations in Eq. (16).

Figure 6:
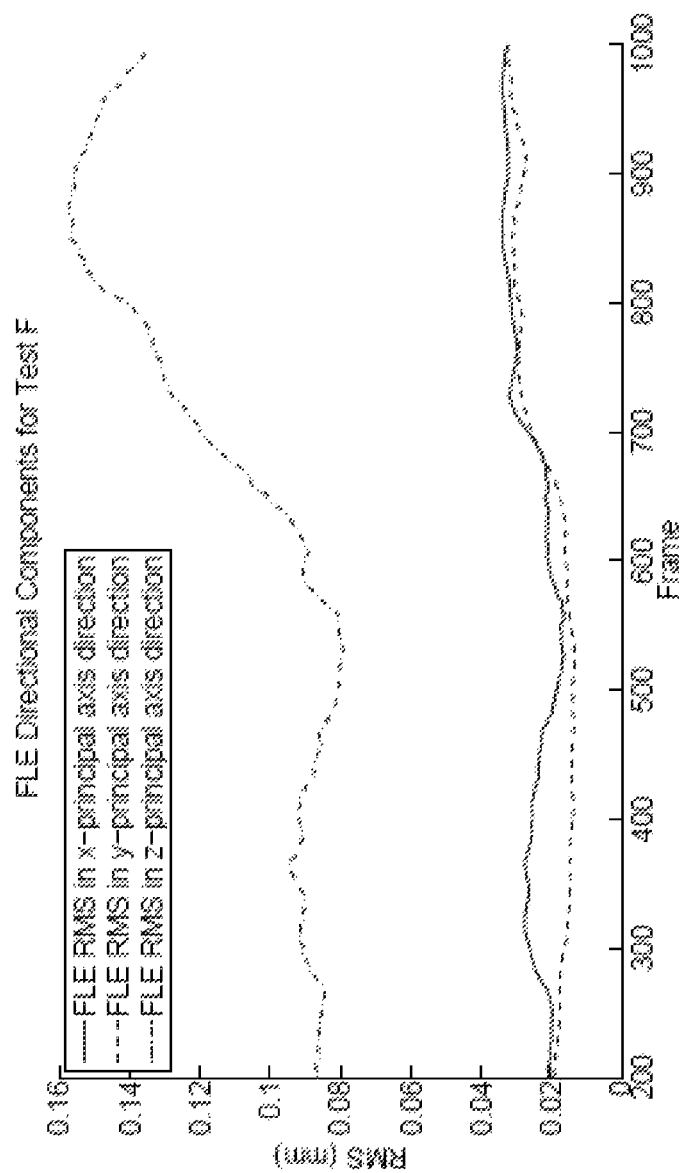
FIG. 6 is an x-y plot showing FLE directional component results for a tracking process using a registration method in accordance with an embodiment.

In FIG. 6, the magnitudes in the three principal directions of the average FLE covariance matrix are given. Here is shown the common behavior of optical tracking systems where one of the components is much larger than the other two directions. The direction of the higher magnitude error is along the viewing direction of the optical tracking system (z-axis of the Polaris Spectra).

Figure 7:
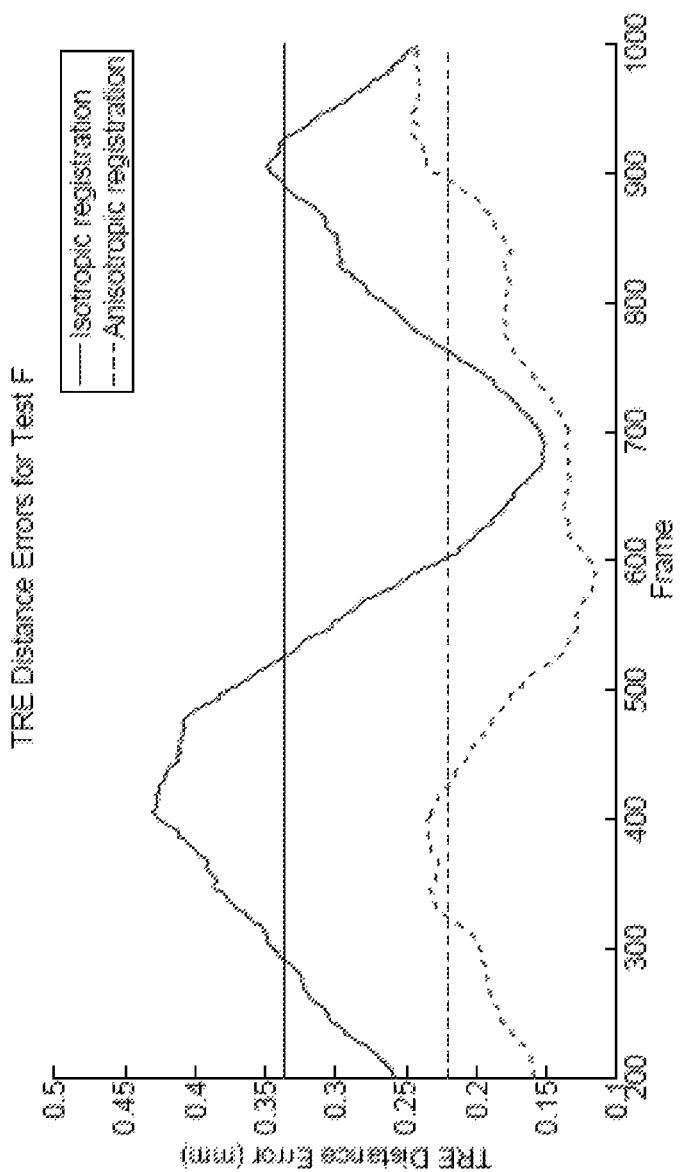
FIG. 7 is an x-y plot showing TRE distance error results for a tracking process using a registration method in accordance with an embodiment.
Figure 8B:
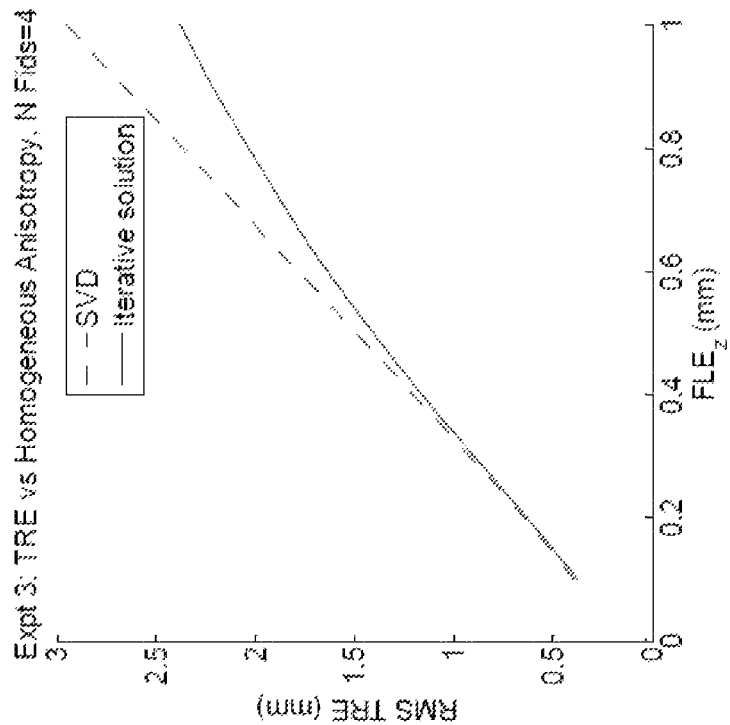
FIGS. 8A-8D show RMS TRE versus $FLE_z$ using two different registrations with FLE in the x and y direction from N (0, 0.1) and N (0, 0.2), respectively, with FLE in the z direction for all the fiducials are from N (0, $FLE_z$), for a number of fiducials=3, 4, 5, and 10.
Figure 8A:
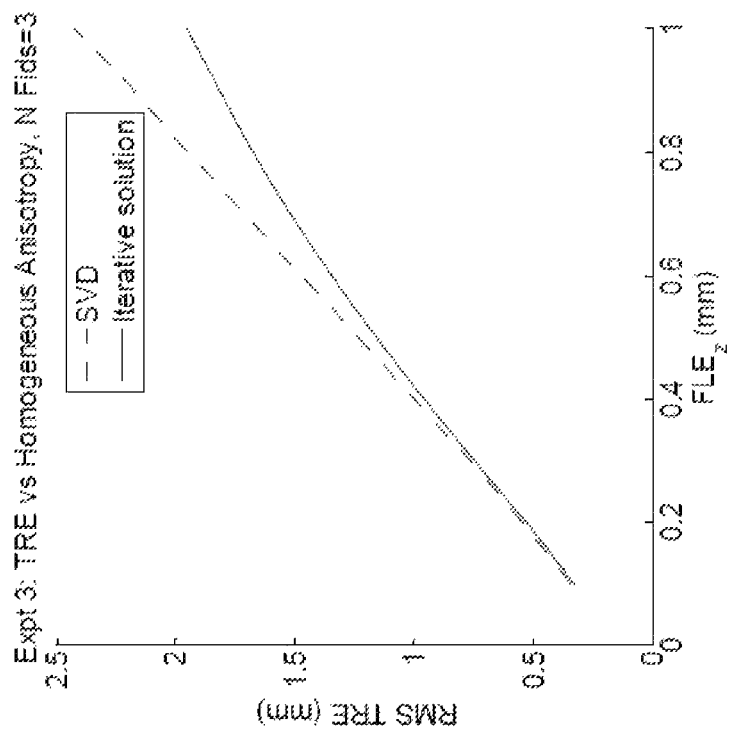
Figure 8D:
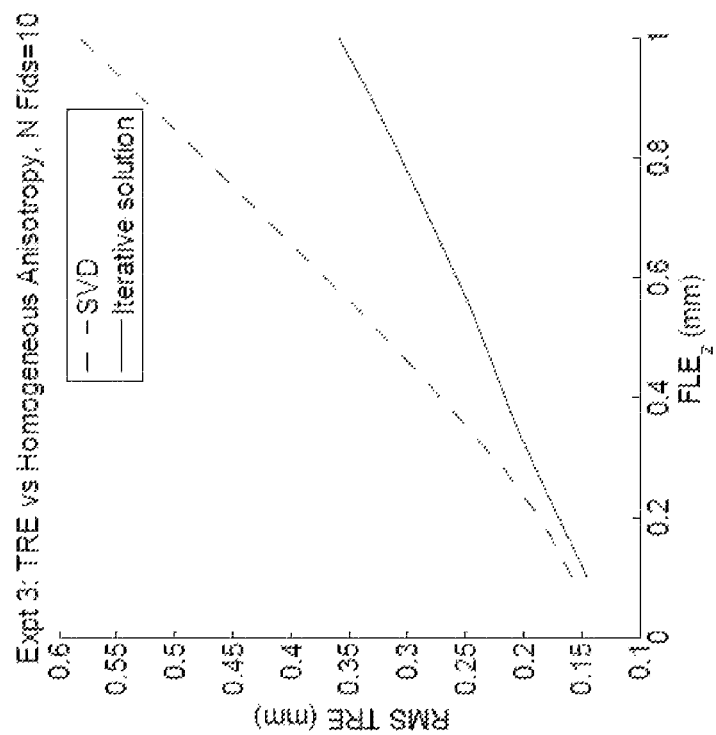
Figure 8C:
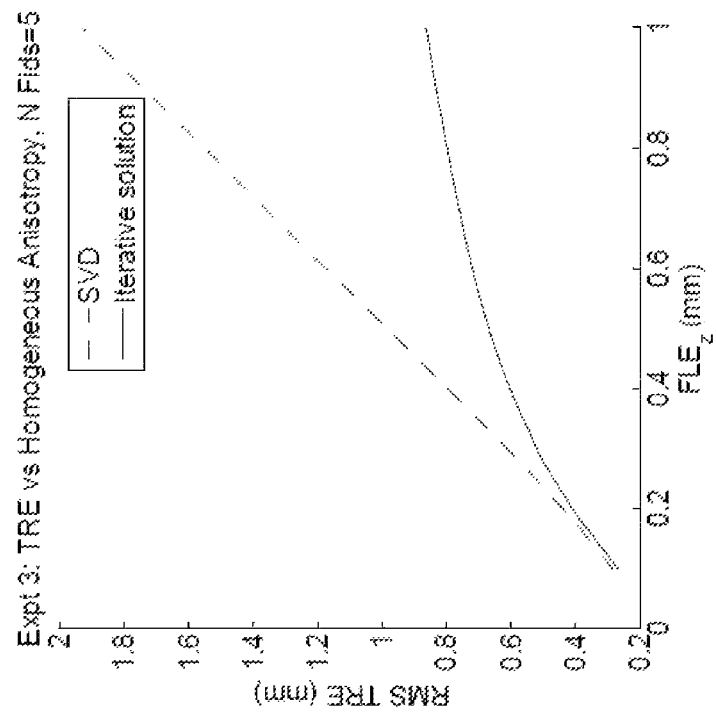
Figure 9B:
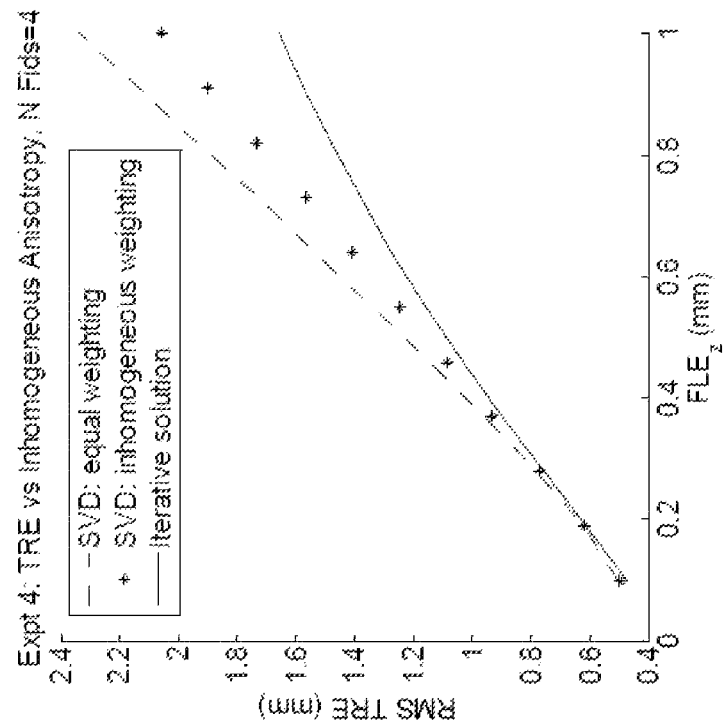
FIGS. 9A-9D show RMS TRE versus $FLE_z$ using two different registrations with FLE in the x and y direction from N (0, 0.1) and N (0, 0.2), respectively, with FLE in the z direction of the first and second fiducials are from N (0, $FLE_z$) and for all other fiducials from N (0, 0.2), for a number of fiducials=3, 4, 5, and 10.
Figure 9A:
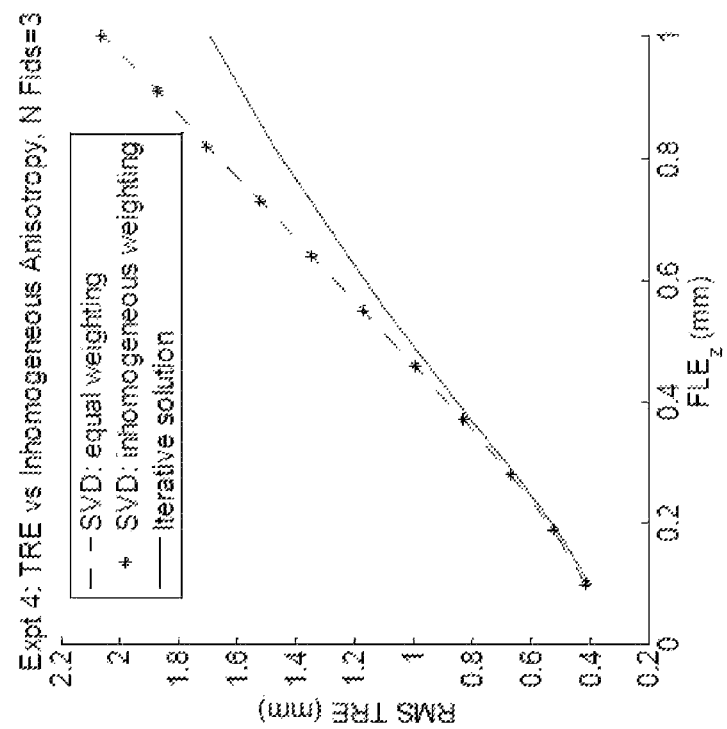
Figure 9C:
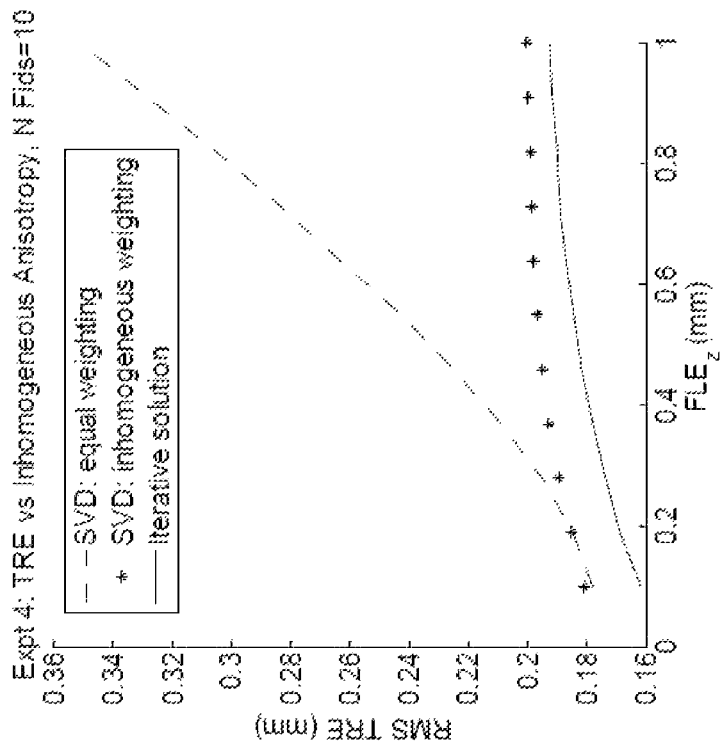
Figure 9D:
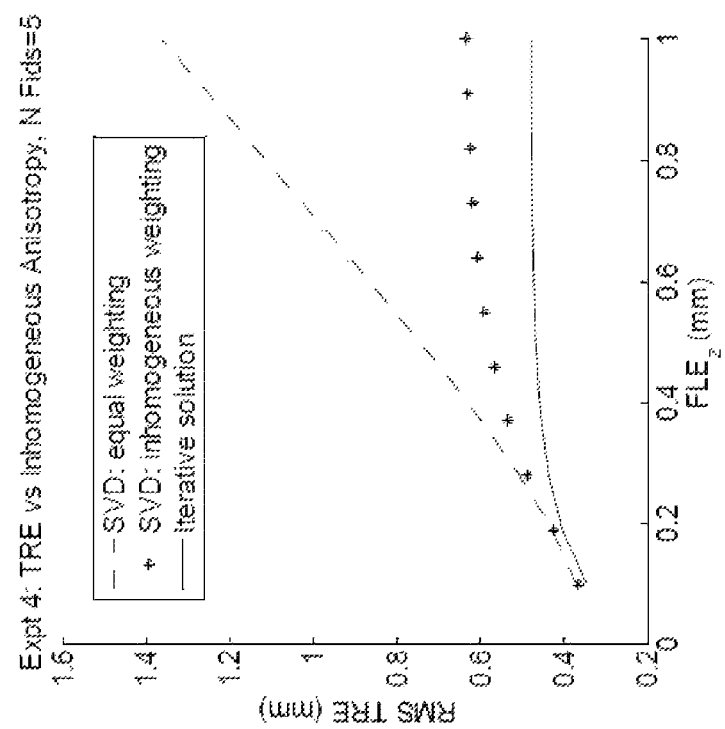

FIG. 7 shows the TRE distance errors at each frame in Test F. As shown in FIG. 7, it is clearly demonstrated that the anisotropic registration provides a better estimate of the target location. The TRE RMS computed over the entire data collection is shown with the horizontal lines. A paired t-test was also performed for this case, showing p<<005, suggesting that the difference between isotropic and anisotropic TREs is statistically significant.

A first registration process in accordance with the various embodiments was tested in conjunction with a registration process using the "ideal" weighting scheme described above with respect It Eq. (19) by performing computer simulations. Four values for N were chosen for the tests: N=3, 4, 5, 10. For each value of N, that number of fiducial locations for X from a cube of edge 200 mm with center at the origin was randomly chosen. The other corresponding fiducial set, Y, was obtained by rotating and translating the X fiducial configuration arbitrarily—10, −20, and 30 degrees rotation about the x, y, and z axes, and a translation of 40, 10, and 100 mm along these axes—then randomly perturbing each position. In this way, the problem was simplified by combining the isotropic localization error in X space into the anisotropic Y space error. X and Y were then registered. Three different registration methods were compared: (1) the closed-form solution with set to 1 for all the fiducials and directions, (2) the closed-form solution with $W_{i\alpha\alpha}$ set to $(\Sigma_{\alpha=1}^N \sigma_{i\alpha}^2)^{-1/2}$ for all the directions of fiducial i, and (3) the proposed iterative algorithm with $W_{i\alpha\alpha}$ defined according to Eq. (19) and a threshold of $10^{-6}$ used for evaluating $\Delta X$. Three random targets were chosen inside a cube of edge 400 mm centered at the origin and the target registration error (TRE) was computed for each registration method. 100,000 iterations of perturbing X to get Y, computing new registration transformations, and computing TRE values were performed to come up with an overall root-mean-square (RMS) TRE value.

Different experiments were performed to study the effect on TRE of using the different algorithms for different cases:

Experiment 1 (homogeneous, anisotropic FLE): A fiducial system with different FLE in the three directions, but same for all fiducials was used for this experiment. FLE in the x and y directions for each fiducial were chosen randomly from N (0, 0.1) and N (0, 0.2) respectively, The FLE in the z direction for all the fiducials were drawn from N (0, $FLE_z$), where $FLE_z$ varied from 0.1 to 1 mm in steps of 0.1 mm.

Experiment 2 (inhomogeneous, anisotropic FLE): A fiducial system with different FLE in all the three directions for certain fiducials and with equal FLE in two directions for other fiducials was used for this experiment. FLE in the x and y directions for each fiducial were chosen randomly from N (0, 0.1) and N (0, 0.2) respectively. The ELF in the z direction for each fiducial was chosen randomly from N (0, 0.2), except tor the FLE in the z direction for the first and second fiducial which were drawn from N (0, $FLE_z$), where $FLE_z$ varied from 0.1 to 1 mm in steps of 0.1 mm.

Experiment 3 (inhomogeneous, anisotropic FLE): A fiducial system with different FLE for all fiducials and directions was used for this experiment. $\sigma_{i\alpha}$ randomly chosen between 0 and 1 for each fiducial and direction. FLEs to perturb X were then chosen randomly from N (0,$\theta_{i\alpha}$). Ten different sets of $\sigma_{i3}$ were used for this experiment.

The results of the simulations of experiments 1, 2, and 3 for each value of N are shown in the figures described below. Each plot compares the RMS TRE values calculated using the three different registration methods for different values of FLE in the z direction. The method based on singular value decomposition described in Algorithm 8.1 by J. M. Fitzpatrick, D. L. G. Hill, and C. R. Maurer, Jr., in "Registration", Medical Image Processing, Volume II of the Handbook of Medical Imaging, M. Sonka and J. M. Fitzpatrick, ed., SPIE Press (2000), was used for the first two registration methods.

FIGS. 8A-8D show the results of Experiment 1. FIGS. 8A-8D show x-y plots of RMS TRE versus $FLE_z$ using two different registrations with FLE in the x and y direction from N (0,0.1) and N (0,0.2) respectively. FLE in the z direction for all the fiducials are from N (0, $FLE_z$). The number of fiducials equals 3, 4, 5, and 10 for FIGS. 8A, 8B, 8C, and 8D, respectively.

FIGS. 9A-9D show the results of Experiment 2. FIGS. 9A-9D shows x-y plots of RMS TRE versus $FLE_z$ using two different registrations with FLE in the x and y direction from N (0, 0.1) and N (0, 0.2) respectively. FLE in the z direction of the first and second fiducials are from N (0, $FLE_z$) and for all other fiducials from N (0, 0.2). The number of fiducials equals 3, 4, 5, and 10 for FIGS. 9A, 9B, 9C, and 9D, respectively.

Figure 10B:
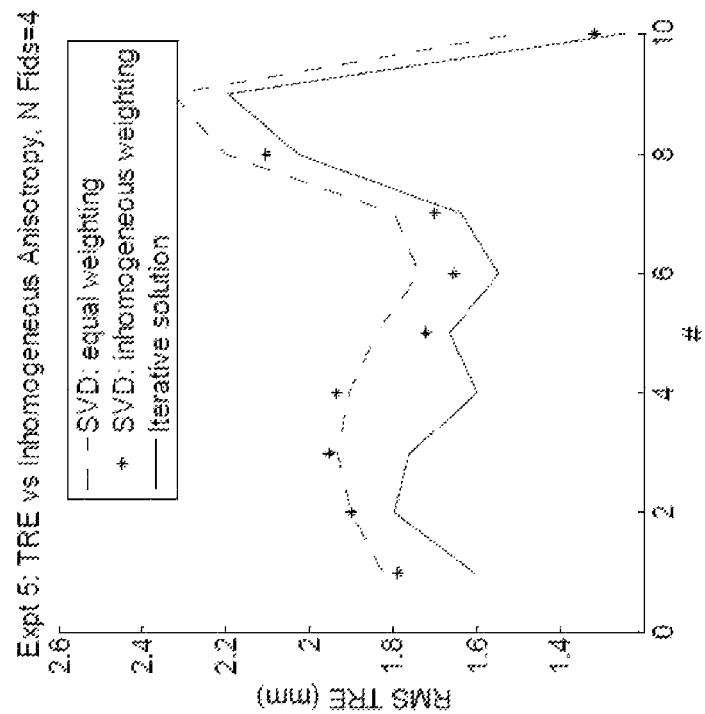
FIGS. 10A-10D show RMS TRE using three different registrations for 10 variations in the FLE in the z direction, where FLE for all fiducials and directions were randomly generated, and for a number of fiducials=3, 4, 5, and 10.
Figure 10A:
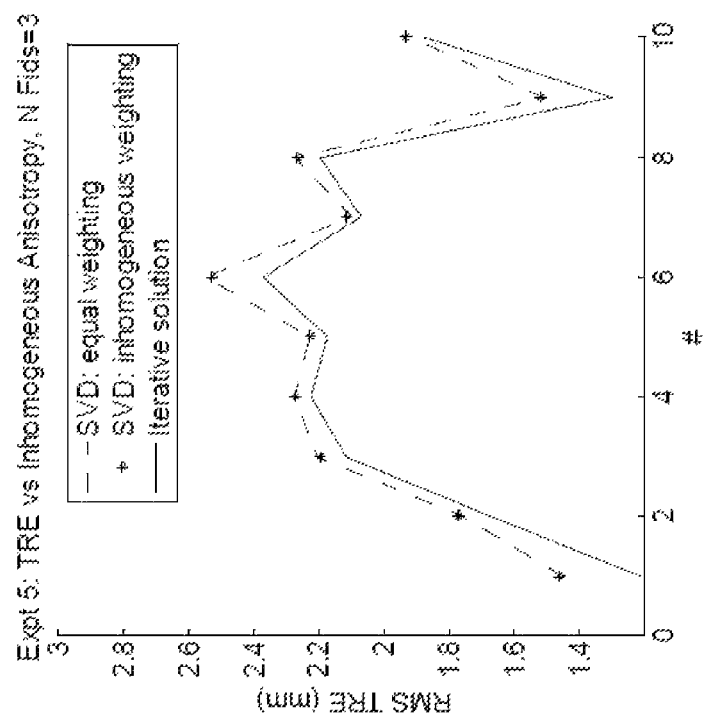
Figure 10D:
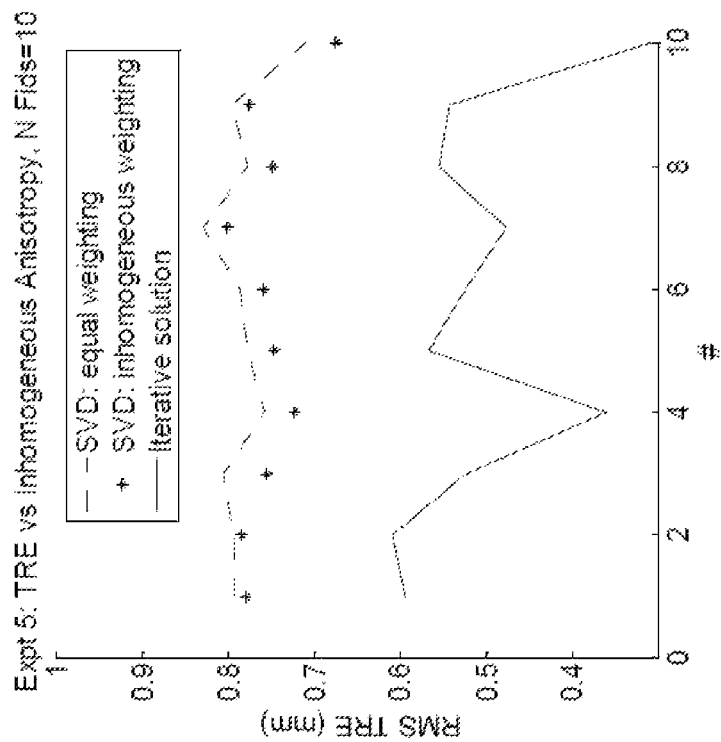
Figure 10C:
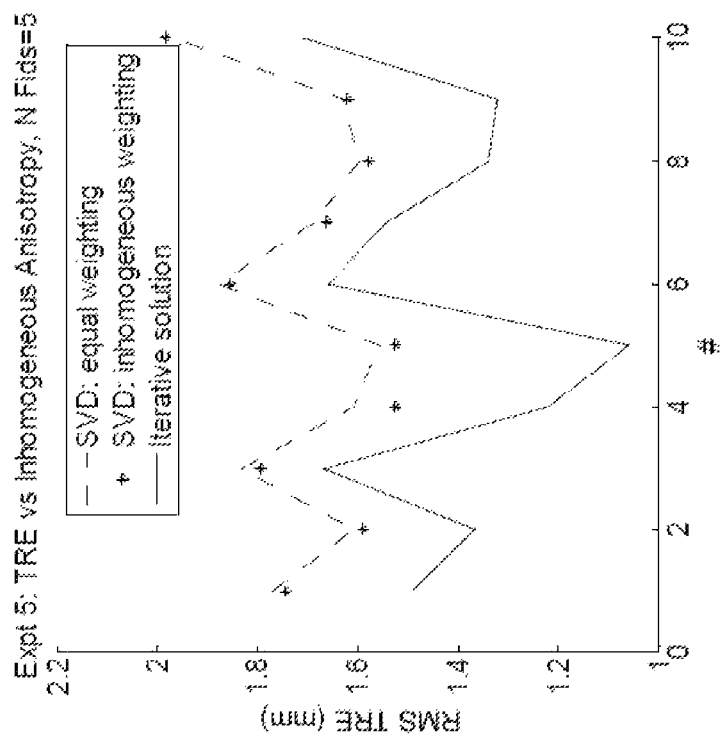

FIGS. 10A-10B shows the results of Experiment 3. FIGS. 10A-10D show x-y plots of RMS TRE using three different registrations for 10 variations in the FLE in the z direction. FLE for all fiducials and directions were randomly generated. The number of fiducials equals 3, 4, 5, and 10 for FIGS. 10A, 10B, 10C, and 10D, respectively.

FIGS. 8A-8D, 9A-9D, and 10A-10D show that the use of proper weighting and iterative approach described herein improves the TRE.

For tracking tools using image-guidance systems, it is important that the registration process does not take long time. The iterative algorithm meets the threshold condition for the fiducial movement quickly. The mean± standard deviation values of the number of iterations taken by the iterative algorithm for different experiments are provided in Table 2, and it is shown therein that they are small.

TABLE 2

Mean and Standard Deviation of the Number of Iterations in Experiments 1-3

| Experiment | Mean | Standard Deviation |
|---|---|---|
| 1 | 11.85 | 2.56 |
| 2 | 10.02 | 2.96 |
| 3 | 13.82 | 0.24 |

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings, In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be father understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A computer-implemented method for performing computer-assisted procedures involving a first set of N three-dimensional points representing locations in a first space of first fiducials and a second set of N three-dimensional points representing locations in a second space of second fiducials corresponding to the first fiducials, where N is an integer greater than 2, the method comprising:
   employing a current rigid transformation to the first set to obtain a current transformed set of N three-dimensional points;
   determining a linearized transformation that minimizes a weighted fiducial registration error between the current transformed set and the second set, the linearized transformation comprising a translation vector and a linearized matrix;
   obtaining an updated rigid transformation based on the current rigid transformation, the translation vector of the linearized transformation, and a rotation matrix that is closest to the linearized matrix;
   applying the updated rigid transformation to the first set to obtain an updated transformed set of N three-dimensional points; and
   if a motion associated with the updated transformed set fails to meet at least one criterion, repeating the steps of determining, obtaining, and applying using the updated rigid transformation and the updated transformed set.

2. The method of claim 1, wherein the motion comprises a relative change between the current transformed set and the updated transformed set, wherein the criterion comprises a threshold value, and wherein the motion fails to meet the criterion when the relative change is greater than the threshold value.

3. The method of claim 1, wherein the step of determining further comprises obtaining a set of N weighting matrices for the weighted fiducial registration error, each of which is multiplied times the difference between one of the N three-dimensional points in the current transformed set and the corresponding one of the N three-dimensional points in the second set.

4. The method of claim 3, wherein each weighting matrix is further based on a weighting matrix for one of the N three-dimensional points in the first space, a second weighting matrix associated with corresponding points in the second space, and a current rigid rotation matrix associated with the current rigid transformation.

5. The method of claim 4, wherein each weighting matrix associated with a point in the first space is based on statistics of a fiducial localization error for the point in the first space, and each weighting matrix associated with a point in the second space is based on statistics of a fiducial localization error for the point in the second space.

6. The method of claim 1, further comprising:
following the step of repeating and prior to the step of obtaining, adjusting the linearized transformation based on the linearized transformation used for obtaining the current rigid transformation.

7. A system for performing computer-assisted procedures, the system comprising:
a memory for storing a first set of N three-dimensional points representing locations in a first space of first fiducials and a second set of N three-dimensional points representing locations in a second space of second fiducials corresponding to the first fiducials, and
a processor communicatively coupled to the memory, wherein the processor is configured for:
employing applying a current rigid transformation to the first set to obtain a current transformed set of N three-dimensional points, determining a linearized transformation that minimizes a weighted fiducial registration error between the current transformed set and the second set, obtaining an updated rigid transformation based on the current rigid transformation, the translation vector of the linearized transformation, and a rotation matrix that is closest to the linearized matrix, applying the updated rigid transformation to the first set to obtain an updated transformed set of N three-dimensional points, and repeating the steps of determining, obtaining, and applying using the updated rigid transformation and the updated transformed set if a motion associated with the updated transformed set fails to meet at least one criterion.

8. The system of claim 7, wherein the motion comprises a relative change between the current transformed set and the updated transformed set, wherein the criterion comprises a threshold value, and wherein the motion fails to meet the criterion when the relative change is greater than the threshold value.

9. The system of claim 7, wherein memory is further configured during the step of determining for:
obtaining a set of N weighting matrices for the weighted fiducial registration error, each of which is multiplied times the difference between one of the N three-dimensional points in the current transformed set and the corresponding one of the N three-dimensional points in the second set.

10. The system of claim 9, wherein each weighting matrix is further based on a weighting matrix for one of the N three-dimensional points in the first space, a second weighting matrix associated with corresponding points in the second space, and a current rigid rotation matrix associated with the current rigid transformation.

11. The system of claim 7, wherein each weighting matrix associated with a point in the first space is based on statistics of a fiducial localization error for the point in the first space, and each weighting matrix associated with a point in the second space is based on statistics of a fiducial localization error for the point in the second space.

12. The system of claim 7, wherein memory is further configured for:
prior to the obtaining and responsive to the repeating, adjusting the linearized transformation based on the solution for the linearized transformation used for obtaining the current rigid transformation.

13. A non-transitory computer-readable medium having code for causing a computer to perform computer-assisted procedures using a method stored thereon, the method comprising:
receiving a first set of N three-dimensional points representing locations in a first space of first fiducials and a second set of N three-dimensional points representing locations in a second space of second fiducials corresponding to the first fiducials;
employing a current rigid transformation to the first set to obtain a current transformed set of N three-dimensional points;
determining a linearized transformation that minimizes a weighted fiducial registration error between the current transformed set and the second set, the linearized transformation comprising a translation vector and a linearized matrix;
obtaining an updated rigid transformation based on the current rigid transformation, the translation vector of the linearized transformation, and a rotation matrix closest to the linearized rotation matrix;
applying the updated current transformation to the current transformed set to obtain an updated transformed set of N three-dimensional points; and
if a motion associated with the updated transformed set fails to meet at least one criterion, repeating the steps of determining, obtaining, and applying using the updated rigid transformation and the updated transformed set.

14. The non-transitory computer-readable medium of claim 13, wherein the motion comprises a relative change between the current transformed set and the updated transformed set, wherein the criterion comprises a threshold value, and wherein the motion fails to meet the criterion when the relative change is greater than the threshold value.

15. The non-transitory computer-readable medium of claim 13, wherein the step of determining further comprises obtaining a set of N weighting matrices for the weighted fiducial registration error, each of which is multiplied times the difference between one of the N three-dimensional points in the current transformed set and the corresponding one of the N three-dimensional points in the second set.

16. The non-transitory computer-readable medium of claim 15, wherein each weighting matrix is further based on a weighting matrix for one of the N three-dimensional points in the first space, a second weighting matrix associated with corresponding points in the second space, and a current rigid rotation matrix associated with the current rigid transformation.

17. The non-transitory computer-readable medium of claim 16, wherein each weighting matrix associated with a point in the first space is based on statistics of a fiducial localization error for the point in the first space, and each weighting matrix associated with a point in the second space is based on statistics of a fiducial localization error for the point in the second space.

18. The non-transitory computer-readable medium of claim 13, the method further comprising:
  prior to the step of obtaining and after the step of repeating, adjusting the linearized transformation based on the linearized transformation used for obtaining the current rigid transformation.

19. A method for performing a computer-guided medical procedure using a first set of N three-dimensional points representing locations in a physical space of at least first fiducial markers on a patient and a second set of N three-dimensional points representing locations in a image space associated with the patient of second fiducial markers corresponding to the first fiducials, the method comprising:
  employing a current rigid transformation to the first set to obtain a current transformed set of N three-dimensional points;
  determining a linearized transformation that minimizes a weighted fiducial registration error between the current transformed set and the second set, the linearized transformation comprising a translation vector and a linearized matrix;
  obtaining an updated rigid transformation based on the current rigid transformation, the translation vector of the linearized transformation, and a rotation matrix closest to the linearized rotation matrix;
  applying the updated current transformation to the current transformed set to obtain an updated transformed set of N three-dimensional points;
  if a motion associated with the updated transformed set fails to meet at least one criterion, repeating the steps of determining, obtaining, and applying using the updated rigid transformation and the updated transformed set; and
  utilizing the updated rigid transformation to direct the medical procedure.

20. The method of claim 19, further comprising:
  prior to said employing, obtaining the current rigid transformation based on a solution for a linearized transformation that minimizes the fiducial registration error between the first set and the second set, assuming that the fiducial localization errors for the first set and the second set are isotropic and homogeneous.

21. The method of claim 19, wherein the step of determining further comprises obtaining a set of N weighting matrices for the weighted fiducial registration error, each of which is multiplied times the difference between one of the N three-dimensional points in the current transformed set and the corresponding one of the N three-dimensional points in the second set.

22. The method of claim 21, wherein each weighting matrix is further based on a weighting matrix for one of the N three-dimensional points in the first space, a second weighting matrix associated with corresponding points in the second space, and a current rigid rotation matrix associated with the current rigid transformation.

23. The method of claim 19, further comprising:
  prior to the step of obtaining, adjusting the solution for the linearized transformation to be an average of the solution for the linearized transformation and the solution for the linearized transformation used for obtaining the current rigid transformation.

24. The method of claim 19, wherein the step of obtaining further comprises computing the rotation matrix based on a singular value decomposition of the linearized matrix.

* * * * *